(12) United States Patent
Brennan et al.

(10) Patent No.: US 10,499,679 B2
(45) Date of Patent: Dec. 10, 2019

(54) IN-LINE SENSOR VALIDATION SYSTEM

(71) Applicant: SmartWash Solutions, LLC, Salinas, CA (US)

(72) Inventors: James M. Brennan, Pleasanton, CA (US); Danny Elmer Lindstrom, Salinas, CA (US); Christopher Michael McGinnis, Seaside, CA (US); Eric Child Wilhelmsen, Milpitas, CA (US)

(73) Assignee: SMARTWASH SOLUTIONS, LLC, Salinas, CA (US)

( * ) Notice: Subject to any disclaimer, the term of this patent is extended or adjusted under 35 U.S.C. 154(b) by 0 days.

(21) Appl. No.: 14/875,144

(22) Filed: Oct. 5, 2015

(65) Prior Publication Data
US 2016/0095475 A1    Apr. 7, 2016

Related U.S. Application Data

(60) Provisional application No. 62/060,325, filed on Oct. 6, 2014.

(51) Int. Cl.
| | |
|---|---|
| *A23N 12/02* | (2006.01) |
| *G01N 27/416* | (2006.01) |
| *B08B 3/00* | (2006.01) |

(52) U.S. Cl.
CPC .............. *A23N 12/02* (2013.01); *B08B 3/00* (2013.01); *G01N 27/4165* (2013.01)

(58) Field of Classification Search
None
See application file for complete search history.

(56) References Cited

U.S. PATENT DOCUMENTS

| | | | |
|---|---|---|---|
| 4,427,772 A | 1/1984 | Kodera et al. | |
| 5,697,366 A * | 12/1997 | Kimball | A61B 5/14557 600/309 |

(Continued)

FOREIGN PATENT DOCUMENTS

| | | |
|---|---|---|
| GB | 2319614 A | 5/1998 |
| WO | 2010045362 A2 | 4/2010 |
| WO | 2011001335 A1 | 1/2011 |

OTHER PUBLICATIONS

European Search Report issued in 15848296.8 dated Apr. 25, 2015.

*Primary Examiner* — Michael E Barr
*Assistant Examiner* — Jason P Riggleman

(57) ABSTRACT

Disclosed is a food wash sensor system that includes a sensor disposed along a fluid flow path that can circulate a wash fluid through the food wash sensor system. The sensor can detect a concentration of an analyte in the wash fluid. The system also includes a reference fluid reservoir including a reference fluid, the reference fluid including a predetermined concentration of the analyte in solution, a delivery system fluidly coupled to the fluid flow path and operable to supply the reference fluid to the fluid flow path upstream from the sensor while maintaining the sensor in place along the fluid flow path, and a control and monitoring system configured to receive a signal from the sensor, the signal indicating the concentration of the analyte in the reference fluid at a first time, and control calibrating the sensor and validating the sensor over time based on the received signal.

13 Claims, 19 Drawing Sheets

(56) References Cited

U.S. PATENT DOCUMENTS

| | | | |
|---|---|---|---|
| 6,438,501 B1 * | 8/2002 | Szecsody | G01N 27/4165 702/100 |
| 7,857,506 B2 * | 12/2010 | Schick | A61M 1/3621 324/441 |
| 2010/0047414 A1 | 2/2010 | Terranova | |

* cited by examiner

TABLE 1

| pH | LACTIC ACID (g) | SODIUM PHOSPHATE MONOBASIC (g) | SODIUM PHOSPHATE DIBASIC (g) | PROPYLENE GLYCOL (g) | AMOUNT OF MIX PER 18 kg CARBOY (g) |
|---|---|---|---|---|---|
| 5 | 8 | 1708 | - | 432 | 54.2 |
| 6 | 100 | 1124 | 304 | 432 | 57.6 |
| 6.5 | 170 | 1468 | 712 | 432 | 61.0 |

FIG. 2

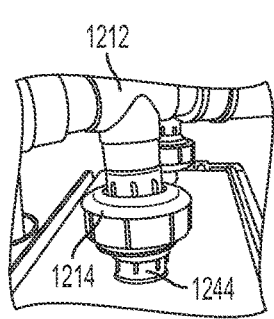 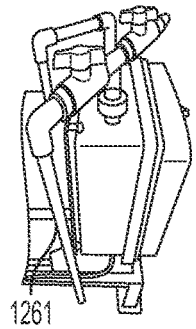 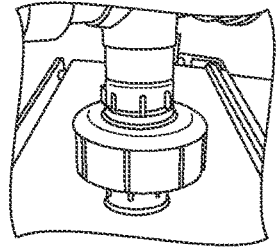 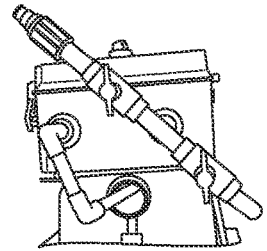
FIG. 12A  FIG. 12B  FIG. 12C  FIG. 12D
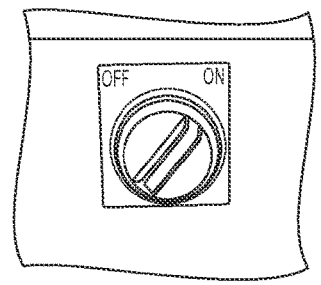 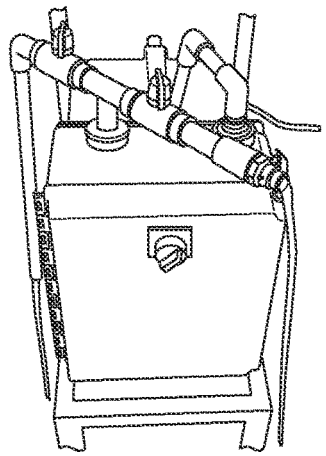
FIG. 12E  FIG. 12F

IN-LINE SENSOR VALIDATION SYSTEM

CROSS-REFERENCE TO RELATED APPLICATIONS

The present application claims priority from Provisional Patent Application No. 62/060,325, filed in the United States Patent and Trademark Office (USPTO) on Oct. 6, 2014. The content of this priority application is hereby incorporated by reference in its entirety.

BACKGROUND

1. Technical Field

The present disclosure relates to in-line sensors for flow monitoring and assuring the validity of in-line sensor response and reporting used during food handling applications.

2. Description of the Related Art

In the not too distant past much of the testing of chlorine in wash water control was done manually with simple test procedures such as test strips or drop-wise titrations. These simple test procedures were suitable for managing swimming pools and seemed to be an appropriate choice for managing the wash systems of processing lines. The test procedures were used to direct manual addition of sanitizers and wash adjuvants to such wash systems. As the desire and need for better control was recognized, however, these simple test procedures proved to be inadequate, lacking both accuracy and precision.

Thus, the food industry migrated to colorimetric procedures utilizing portable meters. This migration provided some improvement. Quantitative data was generated, and control was improved. However, with the current need for validation processes that meet the requirements of the FDA Food Safety Modernization Act (FSMA) and the need to know that a validated process was performed, these colorimetric procedures prove inadequate. They lack the necessary precision and are too slow in monitoring fluid flow path of the process stream. Without better data, it is nearly unmanageable to ensure that the validated process was performed.

There are many different approaches for calibrating in-line sensors that may provide some utility but are subject to limitations and fall short of validating in-line sensor response. For example, a first calibration approach includes assuming that a sensor is accurate by design and fabrication. However, this first calibration approach assumes there is no drift or environmental effects that will cause invalid observations, and that all sensors of a given type generate an equivalent response to the same stimuli.

A second calibration approach includes moving a sensor to an external reference fluid. However, this second calibration approach ignores the effects on the sensor of flow and local depletion of analyte. Additionally, changing the geometry and environment around a sensor can also change the sensor response.

A third calibration approach includes using a reference method to analyze a collected sample of a stream being measured, particularly, measuring a sample removed from a stream and comparing it to a reference. This approach may inappropriately assume that the sample stream is consistent enough that the determined value can be used to calibrate the sensor in spite of a time and space difference inherent in this third calibration approach.

SUMMARY

According to an aspect of an exemplary embodiment, there is provided a food wash sensor system including a sensor disposed along a fluid flow path operable to circulate a wash fluid through the food wash sensor system, and the sensor being operable to detect a concentration of an analyte in the wash fluid, a reference fluid reservoir including a reference fluid, the reference fluid including a predetermined concentration of the analyte in solution, a delivery system fluidly coupled to the fluid flow path and operable to supply the reference fluid to the fluid flow path upstream from the sensor while maintaining the sensor in place along the fluid flow path, and a control and monitoring system configured to receive a signal from the sensor, the signal indicating the concentration of the analyte in the reference fluid at a first time, and control calibrating the sensor and validating the sensor over time based on the received signal, wherein the fluid flow path includes the reference fluid at the first time.

According to an aspect of another exemplary embodiment, there is provided a food wash reference fluid delivery apparatus including a reference fluid that is a solution containing a concentration of detectible analyte, a reference fluid reservoir configured to store the reference fluid, a pump configured to pump the reference fluid from the reference fluid reservoir along a wash fluid flow path at a reference fluid flow rate that matches a wash fluid flow rate past a sensor without moving the sensor relative to the wash fluid flow path, and a controller configured to control the reference fluid flow rate of the pump, reception of a signal from the sensor, analysis of the signal, and transmission of the signal.

According to an aspect of another exemplary embodiment, there is provided a food wash validation method for controlling a food wash sensor system, the method including connecting a delivery system including a reference fluid including a predetermined concentration of an analyte in solution to a fluid flow path of the food wash sensor system along which a sensor is disposed, pumping the reference fluid, using the delivery system, past the sensor while maintaining the sensor in place along the fluid flow path, receiving, at a control and monitoring system, a signal from the sensor in response to the reference fluid passing over the sensor, wherein the signal indicates the concentration of the analyte in the reference fluid at a first time, wherein the fluid flow path includes the reference fluid at the first time, determining calibration by adjusting the sensor until the signal is consistent with known properties of the reference fluid, and determining validation by collecting a plurality of signals over time by repeating the calibration and receiving of the signal, and analyzing the collected plurality of signals.

According to an aspect of another exemplary embodiment, there is provided A food-washing method using a reference fluid, the method including implementing a fluid flow path that is used to clean food using a wash fluid, disposing a sensor along the fluid flow path that is operable to detect a concentration of an analyte in the wash fluid, connecting a delivery system including a reference fluid that includes the analyte in solution to the fluid flow path upstream from the sensor, pumping the reference fluid, using the delivery system, past the sensor while maintaining the sensor in place along the fluid flow path, receiving, at a control and monitoring system, a signal from the sensor in response to the reference fluid passing over the sensor, determining calibration by adjusting the senor until the signal is consistent with known properties of the reference fluid, determining validation by collecting a plurality of signals over time by repeating the calibration and receiving of the signal, and analyzing the collected plurality of signals, and cleaning food using the fluid flow path and wash fluid based on the determined calibration and validation and sensor readings.

BRIEF DESCRIPTION OF THE DRAWINGS

The above and/or other aspects of the present disclosure will become apparent from the following description of exemplary embodiments, taken in conjunction with the accompanying drawings, in which:

FIG. 2 is a table showing different formulae for making bulk batches of pH adjusters in accordance with an exemplary embodiment;

FIGS. 12A, 12B, 12C, 12D, 12E, and 12F shows different views and components of a calibrator that includes an outlet pipe that is arranged and connected as part of the calibrator and then run in a self-priming arrangement in accordance with one or more exemplary embodiments;

DETAILED DESCRIPTION

Figure 1:
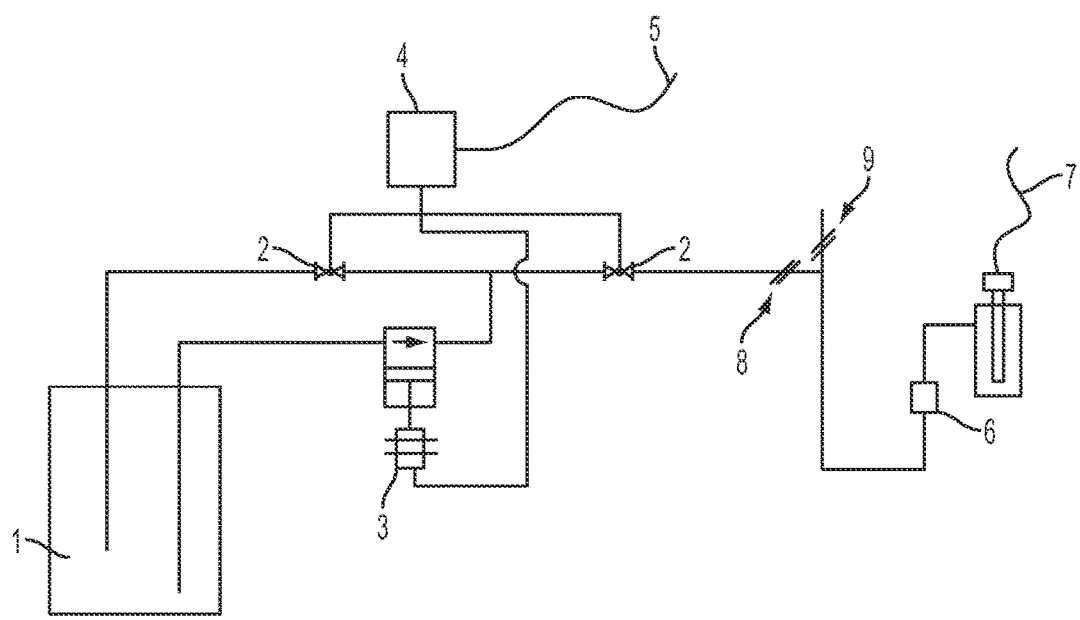
FIG. 1 is a flow regulated reference delivery system in accordance with an exemplary embodiment.

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing operations described is an example; however, the sequence of and/or operations is not limited to that set forth herein and may be changed as is known in the art, with the exception of operations necessarily occurring in a particular order. In addition, respective descriptions of well-known functions and constructions may be omitted for increased clarity and conciseness.

Additionally, exemplary embodiments will now be described more fully hereinafter with reference to the accompanying drawings. The exemplary embodiments may, however, be embodied in many different forms and should not be construed as being limited to the embodiments set forth herein. These embodiments are provided so that this disclosure will be thorough and complete and will fully convey the exemplary embodiments to those of ordinary skill in the art. The scope is defined not by the detailed description but by the appended claims. Like numerals denote like elements throughout.

The following explanation of terms is helpful in understanding the calibration and verification procedures. Calibration may be understood to be a process of comparison under controlled conditions between the readings obtained by a measuring instrument or system and a corresponding measuring standard of high accuracy. Verification may be understood to be the process and objective evidence used to evaluate if a unit, product, or service under testing meets a given set of requirements, specifications, and/or regulations. Said another way, calibration and validation are distinct terms each defining distinct procedures. For example, calibration may be generally understood to be a procedure in which a comparison is made between a standard measurement having a known magnitude or correctness and making an adjustment to a test measurement based on how it compares to the standard measurement. For a typical sensor, a linear response may be assumed with zero intercept. There are multi-point calibration processes that are sometimes not used because the multi-point calibration process is more time consuming.

Validation may be considered a more complete process whereby it may be determined, and therefore known, that the reported values meet some level of precision and accuracy. Validation also involves knowing that the system continues to report true values thereby providing assurance that the generated data can be used for decision making with confidence. Accordingly, validation may be considered a more complete process requiring assessment of in process measurements and a history of performance against known materials.

Calibration/verification may be understood to be a procedure and objective measurements that confirm that a unit's (e.g. pH and Cl sensors) current calibration settings remain valid. Validation may be understood to be the establishment of documented evidence that a process, system, and/or activity will produce consistent results that meet pre-determined specifications. Calibration/verification frequency may be defined as the frequency with which chlorine electrodes need to be monitored and calibrated on a regular basis to maintain the desired accuracy and precision of measurements. Calibration/verification frequency may be determined for each individual electrode as each electrode is unique and subject to different operating conditions that may affect its performance.

Factors to consider when defining the calibration/verification frequency are: allowable tolerance range; required measuring accuracy and precision; environmental conditions which may affect performance of the electrodes; historical calibration stability trends; quality assurance; customers and food safety requirements; impact of non-compliant calibration verification checks/data; and cost of the calibration/verification program.

Reference will now be made in detail to a food wash sensor system, which may also be called an in-line sensor validation system, and method for operating the food wash sensor system in accordance with the exemplary embodiments, examples of which are illustrated in the accompanying drawings, wherein like reference numerals refer to like elements throughout.

The above noted need for better and validated data has provided a starting point for providing a food wash sensor system and process as described. Additionally, the precision laboratory methods for chlorine analysis such as those described in standard methods of water analysis are not compatible with the speed requirements for control and are not suitable for use on the plant floor or in a food processing area where contamination might occur. This recognition lead to the idea of a validated sensor reading used for both monitoring the process and for providing input for control.

According to one or more exemplary embodiments, there is provided a food wash sensor system, also known as an in-line sensor validation system, having a flow regulated reference delivery system, a reference fluid that may also be called a reference material and/or a family of materials, and a control and monitoring system assembly. Each of these components individually may be implemented by one or more distinct exemplary embodiments, each of which may improve the regulation of in-line sensor response, and in concert they may afford the validation for managing critical control points such as those for assuring food safety.

Each of the three components of the validation system can be embodied in a variety of ways depending on the level of precision and accuracy desired and the level of automated involvement that can be implemented. Additionally, the desired confidence for data validity may be selected. The system may provide the components as a single integrated unit, as three distinct components, or a combination thereof. Alternatively, a portion of these components may be included with other equipment such as the systems delivering materials to a fluid flow path of a process stream. For example, systems adding sanitizers to a wash system is a clear example of such equipment systems.

The specific elements of each component can be physically packaged for a specific application without changing the functionality. In some exemplary embodiments a controller or an operator will provide some portions of the control and monitoring function. An operator will generally not be able to provide the almost immediate validation of an automated system and will necessarily examine less data, which may be acceptable for some applications. However, given that labor is an ongoing expense and source of error that can be controlled with greater automation, human intervention in the control and monitoring function may be reduced. With this in mind, descriptions provided herein span a range of complexity and automation to guide implementation over a broad range of possible exemplary embodiments to yield different confidence levels, different precision levels, and different levels of accuracy.

According to one or more exemplary embodiments, a food wash sensor system for calibration and validation taught herein can be applied to any sensor used to monitor a fluid flow path of a process stream. Process streams are generally gas or liquid and have localized homogeneity to allow generation of useful sensor responses. Powder flows of solid material might be amenable to this approach if the degree of local homogeneity is confirmed. Sensor responses are a metric that is interpreted by a control and management system to yield an intensive characteristic of the process stream.

According to one or more exemplary embodiments, a food wash sensor system for calibration and validation may include sensors where the sensor response is impacted by flow and other process-related variables that are controlled with the sensors in their original place. Sensors that can be reconditioned or refreshed in situ are of particular interest as the control and monitoring system can control the timing and duration of these refresh cycles on an as needed basis. Galvanic sensors and other sensors that consume analyte are a particular and important class of sensors that are sensitive to flow which may be implemented in one or more exemplary embodiments. Analyte depletion requires flow compensation or flow control for reliable measurements.

According to other exemplary embodiments, other sensors may be implemented. For example, the system may include sensors for oxidants such as chlorine including hypochlorous acid and hypochlorite, chlorine dioxide, and the various forms of active oxygen including ozone, hydrogen peroxide and peroxyacids which are members of this set of sensors for oxidants. Oxygen is a much weaker oxidant but is also often detected by a galvanic sensor which has flow dependence. These classes of sensors are candidates for use in a food wash sensor system for calibration and validation in that they are used to control critical process parameters in food processing and particularly in fresh produce processes. If any sensor is monitoring a critical process variable, validation becomes critical particularly where safety is involved such as in a food processing operation.

FIG. 1 is a schematic drawing of a food wash reference fluid delivery system that may also be called an apparatus with flow regulation according to an exemplary embodiment. The food wash reference fluid delivery system includes a reference fluid reservoir (1), a manual or electronically controlled flow matching valve(s) (2), a pump (3), a flow control panel (4), an auxiliary external device connection (5), a flow monitoring device (6), a sensor to be validated (7), a quick connect or line connection for validation device solution flow (8), and a quick connect or Line Connection for normal sample flow (9)

Referring now to the exemplary embodiment in more specific detail, in FIG. 1 the basic elements of the food wash reference fluid delivery system are shown, which is a first component of a validation system. Taking the elements that make up the food wash reference fluid delivery system in order, the reference fluid reservoir (1) has several specifications that define its parameters. For example the size of the reference fluid reservoir (1) is a first specification. In accordance with an exemplary embodiment, the reference fluid reservoir may have a capacity of 20 liters. This may provide a good balance between validation capacity and portability for liquid reservoirs. Larger volumes become difficult to mix and relocate when using a portable delivery system. However, it can be appreciated that the capacity of the reference fluid reservoir may be substantially smaller or substantially larger depending on a user's desired implementation while still providing the desired use for validation. In one embodiment, about four liters of reference fluid is used per cycle to manually confirm calibration or adjust a sensor at the scale illustrated by the delivery system in FIG. 1. Therefore, a 20 liter reservoir has the capacity to hold enough reference fluid for four or five calibration confirmations or sensor adjustments.

Further, according to an exemplary embodiment, the reference fluid reservoir (1) is fabricated from a material and in a way to contain and protect the reference fluid. Additionally, analyte loss is avoided or substantially lessened such that the loss occurs at a known rate. Many of the polymeric plastics are generally suitable with polyethylene and polypropylene being particularly useful by being inert to a broad range of analytes including the oxidants listed above when these oxidants are used at modest concentrations appropriate for food processing. According to another exemplary embodiment, when a gaseous reference fluid is used, for example in a gaseous process stream, the reference fluid reservoir (1) is implemented as a pressure vessel.

The flow matching valves (2) are implemented for controlling reference fluid flow to a sensor (7) which are controlled either manual or electronically. The flow matching valves (2) can be controlled by an operator input or by some form of automation. The flow matching valves (2) themselves can be of various designs so long as they provide flow control over the desired range of flows. For example, the flow matching valves (2) can be implemented using needle valves that have proven especially useful for controlling flows around 1 liter per minute which helps avoid the impacts of analyte depletion. The flow matching valves (2) work in concert with an in-line flow monitoring device (6) that can be used to compensate for flow variance when fluid flow is not constant and may provide higher precision when desired. An in-line flow monitoring device (6) can also be used to remove noise associated with pulses in reference fluid flow generated by a pump (3). Such compensation can be done while reference fluid is running through the fluid flow path of the process stream past the sensor, or while the wash fluid is running through the fluid flow path of the process stream past the sensor. The compensation of the fluid flow path when reference fluid and when wash fluid is present provides for improved comparisons between responses with these two materials. Alternatively, rate observance that includes detecting, recording, and reporting flow rates during reference fluid and wash fluid running is an alternative to flow rate control. Further, when both compensation and rate observance are employed, greater precision may be obtained.

The pump (3) is used to provide pressure to induce reference fluid flow through the fluid flow path of the process stream. Process flow of wash fluid through the fluid flow path may be achieved with a different pump or source of pressure. According to an exemplary embodiment, the pump (3) generates 5-10 psi. A large pump and a throttled by-pass may be used to regulate pressure and flow through the sensor in addition to the flow control valves (2). For this design a rotary lobed pump may be used, but other approaches for generating fluid or gas flow can be used such as a pressure vessel for gases or other types of pumps for liquids. Precision and accuracy are affected by the consistency of the flow rate. Further, pulses in flow rate inject noise. This noise may limit the precision and accuracy of the sensor system if not accounted for. In some systems, pulse dampening may be implemented at the expense of increased system volume.

The flow control panel (4) and the auxiliary external device connection (5) are connected to a control and management component of the food wash sensor validation system. The flow control panel (4) regulates the pump (3). This regulation can be a simple switch or can be a more sophisticated control. For example, the control may be similar to that which is used with a variable speed pump. The reference delivery system collectively delivers the desired flow of reference fluid to the sensor (7), and the flow control panel (4) regulates the pump (3) that provides the motive force for this flow. The flow control panel (4) may be additionally connected to the manual or electronically controlled flow matching valves (2). The auxiliary external device connection (5) provides for two-way flow of information from the control and management component. This connection allows delivery of reference fluid on an as needed basis.

According to an exemplary embodiment, the sensor (7) may be compatible with the fluid flow path of the process stream, or the fluid flow path of the process stream may be conditioned to be compatible with the sensor (7). This compatibility includes the geometry and working environment. Filtration is one way to increase this compatibility. Sometimes, in addition to increased compatibility efforts, remediation is required. Such remediation can include mechanical scrubbing with air or other means or chemical means such as reversing polarity or changing the potential applied to the sensor. Validation requires that compatibility be managed. This management is performed by the control and management component.

In accordance with an exemplary embodiment a quick connect or line connection for reference fluid flow (8) and a quick connect or line connection for normal sample wash fluid flow (9) may be included that allow for selection of either the reference fluid or the wash fluid to flow through the sensor (7) without displacing the sensor, or more specifically, without changing the geometry or environment of the sensor (7). In accordance with another exemplary embodiment, these connections could be replaced by a two-way valve while achieving the same functionality. Such a valve could be used to automate control of the reference delivery process. Using a valve may limit functionality when the same reference delivery system is used with multiple sensors where portability is needed. This situation sometimes occurs in a food processing facility where multiple lines utilize the same type of sensor for process control. In an exemplary embodiment, long runs of tubing or pipe between the reference fluid reservoir and the sensor are avoided in order to control the volume for calibration.

According to one or more exemplary embodiments, the reference fluid is an important element used in the calibration process and the validation process. For example, if the reference delivery system is considered to be the heart, then the reference fluid is the blood. The accuracy of all determinations by the sensor relies on the accuracy of the reference fluid. Multiple inaccurate measurements due to an inaccurate reference fluid will not cluster around the true value of the response. In this case, repeated measures will not provide a better understanding of the true value.

There are several attributes to consider regarding the development and selection of a reference fluid. First and foremost is the precision and accuracy of the reference fluid. Given that the reference fluid will be used to calibrate and validate the sensor, in one or more embodiments the reference fluid may need to be provided with three to five times greater precision and accuracy as compared to the normal wash fluid sample flow. This can be determined by a comparison of a standard error for the reference fluid compared to a standard error needed for the wash fluid of the process stream. In one or more embodiments, the standard error may include error in sensor response and error due to process stream inhomogeneity. This value for greater accuracy and precision may be obtained by applying a reference method. For example, the AOAC association and other such bodies are a good source of such reference methods. These methods may deliver three or four times greater accuracy and may not generally limit the validation process.

The second attribute is the stability of the reference fluid. In accordance with one or more exemplary embodiments, six months stability has proven to be sufficient for most applications. To achieve this shelf life, some components may be stored separately. According to an exemplary embodiment, the materials may be stored in a dry form. There is a natural inclination to want to store material as dry powders, but the dry forms of some analytes can lack the sufficient homogeneity and stability. For example, calcium hypochlorite does not make a good reference for chlorine for these reasons. In accordance with another exemplary embodiment, a concentrated solution of sodium hypochlorite is an alternative choice that may provide better homogeneity and stability as compared to dry calcium hypochlorite. In some applications, the exchange of some precision and accuracy for convenience may be acceptable.

In accordance with one or more exemplary embodiments, reference fluid portability, ease of preparation, and costs are considerations to be balanced. Overall cost is impacted commonly due to shipping costs associated with the weight and volume of constituents. The cost of the constituents of the reference fluid also plays a role in the overall cost depending on the constituents selected. Although there are exceptions, most analyte constituents are used at modest concentrations, typically less than 100 ppm. When concentrations increase, for example sugars, the cost for the constituents tend to decline as these materials tend to be bulk materials. It is important to include any known interfering constituents for the calibration to be effective. Solvents may be the exception because solvents may be used in larger concentrations making up the largest portion of constituents of the reference fluid. The solvent should be of sufficient purity to allow preparation of the reference fluid. The cost and availability of this solvent must be weighed against the weight of the solvent in shipping. It will usually be less expensive to prepare a concentrate and dilute with the appropriate solvent at the time of use. This approach is generally preferred due to the ready availability of deionized or distilled water which is the most common solvent. For cost reasons it is tempting to use a potable water source as the solvent. This is acceptable if the potable water source does not already contain the analyte or contains a known amount within acceptable bounds. For example, potable water will typically contain 0.2-4.0 ppm of chlorine which may add substantial uncertainty to any reference fluid for a chlorine sensor if constituted with typical potable water.

Ease of preparation is important because such preparation activities tend to be implemented using devices that cannot track or show accuracy measurements such that a user cannot appreciate or understand the accuracy of their effort. Additionally, if a preparation procedure is too complicated, there materializes a potential that short cuts will be taken or that procedural errors or inaccuracies will occur. For example, a need for quantitative transfers to move constituents into the reference fluid reservoir is a common complication. For many systems it may be inadequate to simply pour the constituent into the reservoir. Instead, solvent must be used to rinse the delivery container several times to effect a complete transfer. It has been noted that a container that opens at both ends such a bag or pouch allows convenient flow through transfer providing some ease of preparation.

For the reference fluid to be compatible with the control and monitoring component, the statistical precision and accuracy should be known. This may be achieved with multiple determinations by a reference method using a reference standard. Further, using error propagation calculations, it may be possible to calculate mean and standard deviation of the reference fluid which determines the limit of a validation effort.

Another component of a food wash sensor system for calibration and validation is a control and monitoring system or assembly. In accordance with an exemplary embodiment, the complexity of this assembly is a function of how many mistakes can be tolerated and how big those mistakes can be. All systems have at least some theoretical potential to leak. One must decide how close to zero this needs to be for the process being monitored. Said another way, threshold values above and below an ideal measurement, as well as tolerances in both size and quantity, should be set and monitored by the control and monitoring assembly. These threshold and tolerance values within which measurements may be considered acceptable may be set for a given system and/or sensor. Further, this exercise can be rendered inaccurate if either the sensor is incapable of the desired precision and accuracy or the reference fluid lacks the necessary precision and accuracy. In either of these cases, the validation process can confirm these inadequacies.

Specifically, in accordance with one or more exemplary embodiments, when the food wash sensor system is functioning as a validation system, a control and monitoring assembly may perform many functions. For example, some of these functions may include, but are not limited to, determining a calibration status of a sensor, calibrating the sensor, and identifying when to next test the calibration status of the sensor. Another function the control and monitoring assembly, or system, may perform and include, but is not limited to, is determining if the process is in its nominal range and if the variance is nominal. Additionally, another function the control and monitoring system may include, but is not limited to, is determining if the sensor needs to be regenerated or cleaned and running the regeneration procedure. Finally the control and monitoring system may include, but is not limited to, monitoring the control status of a process as the collected information may be used to control the process, including, but not limited to, the addition of adjuvants and additives such as sanitizers and regulating product flow.

These functions use historic data collection, analysis, and data based implementation and/or action. The control and monitoring assembly may use one or more functions to identify deviations as early as possible to assure the reliability of data generated by the sensor and information developed from this data. The recursive nature of these functions is linked to the ability to properly present a reference. This suite yields data validation and assures the reliability of the process monitoring.

In accordance with an exemplary embodiment, a food wash sensor system that calibrates and verifies a sensor can be used in conjunction with, and therefore described in the context of, a particular system and method of operating a food wash process stream. Particularly, the context and method may be a monitoring of process parameters in a dual tank produce wash system in a multi-line processing plant. Such a context and method may have the advantage that it includes several types of sensors illustrating different approaches to calibration and verification processes. Two chemical parameters, pH and chlorine levels, are process parameters for food product safety that should be monitored and adjusted. Temperature, a physical parameter, is also monitored for product quality and can impact the readings of the other sensors, particularly if temperature is out of desired bounds. The operation of dual tank systems to process a leafy green such as chopped lettuce includes several features including fouling, interdependence of signal response, chlorine demand, spatial variance, and the need to adjust the process stream based on the sensor responses.

An illustrative processing plant in which the disclosed exemplary embodiments may be implemented will now be described. Particularly, the processing plant, which may be a smaller and more homogenous system than other operating facilities, may contain four dual tank lines with each tank having the same set points. For example, the set points may be: pH 5, 15 ppm chlorine, and 34 degrees F. In accordance with one or more exemplary embodiments, in actual practice these set points and their associated control parameters would be a function of the validated processes for each product that is being processed and therefore the values may vary according to the particular produce being processed. Additionally, larger actual processing plants would also potentially have many more lines that would be used to process many different products. Further, some lines process two or more different products during a shift. Process control will typically keep the process lines in some small allowed range within the practical operating range of between 32 and 45 degrees F. with pH values between 3.5 and 6.5 and free chlorine levels between 0 and 20 ppm. From a food safety perspective, there is a lower limit at 1-2 ppm for chlorine where cross contamination becomes a greater concern. Upper limits for chlorine are usually driven by quality factors but can be limited by regulatory constraints in some exemplary embodiments. The lower limit for temperature is usually limited by the risk of freeze damage. Lower temperatures also increase energy costs. The set points and the processing parameters may vary with equipment type and product. The water may be recirculated in each tank with make-up water for the primary tank, the dirtiest, coming from the secondary tank, and new water being added to the secondary. A final water curtain after the secondary is often used to provide make-up water for the secondary. The pH, chlorine levels, and temperature of each of these tanks must be controlled to mitigate the risk of cross contamination to the extent possible.

For the temperature sensors, a thermistor may be implemented. Further, a thermistor may be included in the pH sensor for temperature compensation. The response from this sensor is retrievable for the verification process. In accordance with an exemplary embodiment, the thermistor is more stable and less prone to problems than the pH probe or sensor or the chlorine probe or sensor. Also, fouling will not change the values reported by this sensor but can increase response time. A small thermal mass associated with the sensor will reduce response time allowing the rapid detection of any change. However, given the volumes of water involved, generally over 1000 gallons in a tank, the thermal mass of the system is large and temperature change is slow.

For the pH sensors, a food-grade gel-type electrode probe may be selected as robust and durable and therefore capable of being validated. This probe was selected as compatible with good manufacturing practices (GMP) and when properly managed as described below, it can yield reliable data. This sensor is potentiometric and not galvanic and therefore less sensitive to geometry and flow rate than the chlorine sensor. As discussed below, this allows calibration with a more traditional approach, but data verification and validation is still implemented to monitor, adjust, and confirm proper operation and detection. Alternatively, according to one or more embodiments, other pH sensors may be used that provide similar data and reliability metrics.

For the chlorine sensors, a probe designed to respond to hypochlorous acid as opposed to hypochlorite ions may be selected. For example, a potentiostatic discharging electrode probe with cleaning cycle which responds to hypochlorous acid may be selected as robust and durable and therefore capable of being validated for one or more exemplary embodiments. Hypochlorous acid is reported to be the most effective antimicrobial among the various forms of chlorine found in solution. However, hypochlorous acid is in equilibrium with diatomic chlorine, hypochlorite and various forms of bound chlorine including mono-, di-chloramine. This type of sensor probe is galvanic and the sensor response is highly sensitive to flow rate due to substrate, chlorine in this case, depletion. Accordingly, the flow calibration procedure disclosed below may be implemented. This particular probe was selected as compatible with GMP, as less subject interferences than a traditional oxidation—reduction probe (ORP), and is more tolerant to the wash water system with proper management as described below. However, in one or more embodiments an ORP sensor may be implemented. Nevertheless, the small portion of the process streams that contacts a sensor probe should be dumped to the floor. According to one or more other exemplary embodiments, it will be appreciated that other sensors may be used as alternatives to the chlorine sensor for monitoring alternative process streams.

One or more of three different approaches to calibrate three types of sensors reflecting the sensitivity to flow, geometry, and other factors that affect sensor response may be implemented. For the thermistor sensors, calibration may be mostly a confirmation of the factory calibration. Temperature is a physical attribute that is not affected by the factors that are problematic for the other two types of sensors. Particularly, use history and fouling may not be considered as significant factors for temperature sensors. Calibration, or confirmation of calibration, is done by comparison of readings for a solution from a reference thermometer. In some cases it may be appropriate to do a two-point calibration with two temperatures spanning the range of interest as done for pH.

For pH sensors, the operating environment is more complicated in that response is affected by temperature and the probe is subject to fouling. Thus, the pH probes should be calibrated frequently to avoid drift. Using two reference fluids, pH 4 and pH 7, to perform two-point calibration may be used. A person skilled in the art will recognize these as red and yellow solutions. By alternating between these two reference fluids, one adjusts the intercept and slope of the response to achieve calibration. These solutions should either be at the temperature of operation, or there should be a validated temperature compensation in place. Thus, one or more thermistors may be included in pH probes. However, this calibration process may lose effectiveness when the pH probe has exceeded its useful life and is no longer fit for use. Fortunately, pH probes are largely unaffected by flow and geometry so more sophisticated calibration may not need to be implemented in this system. Fouling and electrolyte loss still occur and require prompt attention to avoid erroneous data.

For chlorine sensors, the operating environment is more complex. This complexity drove the development of the food wash sensor system for calibration and validation. Particularly, for calibration of the galvanic chlorine sensors, a delivery system for the reference fluid is used to match the process flow rate. The pH of this material should match the pH of fluid flow path of the process stream, or the calibration will likely be invalid. Furthermore, the reference fluid should be of known chlorine strength and be produced in a manner that controls other interferences. Organic material in the reference fluid is a particularly disruptive interference causing some mixture of chlorine loss or binding which renders the reference fluid inaccurate potentially invalidating all data until there is a new calibration.

In accordance with one or more exemplary embodiments, the reference fluid for the illustrative processing plant may be mostly phosphate buffers that mimic the acidification of a wash adjuvant used in wash processes and deliver chlorine to generate chlorine probe response. Other reference fluids could be used or would need to be used for different processes. These alternatives are discussed later. Given the desire to ship and store these reference fluids, dry pH adjusters may be made that can be added to deionized water with small aliquots of standardized chlorine to yield the reference fluid. The constituted reference fluids disclosed in this embodiment may be inherently unstable and should be used within 4 hours of preparation for precise calibration. Other more stable reference fluids may also be used. The pH adjusters should compensate for the alkalinity of the standardized chlorine solution, specifically, a solution of sodium hypochlorite.

In accordance with an exemplary embodiment, to make an 18 kg unit, about 18 liters, of reference fluid one takes and tares a clean dry container of sufficient size. For example, a polypropylene carboy may be used. Next, about 10 kg deionized water is added to the container to avoid solids settling to the bottom. The pH adjuster is then transferred to a clean 1 liter bottle. Water is added and then may be shaken or stirred to dissolve. The resultant solution is added to the original container. The chlorine solution is then quantitatively transferred to the carboy. Then mixing well and filling to 18+/−0.010 kg net weight follows. Then mixing well with about 5 minutes of agitation should follow. The accuracy of the final weight is important for generating a precision reference fluid. It is recognized that one can correct for dilution deviations to achieve the desired precision and may adjust the order of the above operations and the particular amounts while maintaining similar proportions. According to another exemplary embodiment, particularly in practice, this preparation is done by less skilled workers, and tracking variations in dilution would be another detail to be tracked and has been found to be an unwarranted complication. Either approach may yield a solution of known concentration of an analyte, specifically, a chlorine concentration.

One or more exemplary embodiments may include the use of one or more of the formulas for making bulk batches of three different pH adjusters which are included in Table 1 found in FIG. 2. The materials may be weighed out and blended in a V-blender. The resulting paste may be parsed into packets sized for making 18 kg batches. It should be noted at this scale that losses are 2-4% depending on the patience of the worker.

The chlorine solutions for the reference fluids may be made by diluting a standardized sodium hypochlorite solution to yield the desired reference fluid. For example, in accordance with an exemplary embodiment, to make a 13 ppm reference fluid, 100 g of 2350 ppm chlorine is added to the carboy above. These solutions should be stored in tightly closed inert containers such as polyethylene or glass. The polyethylene bottles are more compatible with GMP requirements for a food plant.

In accordance with one or more exemplary embodiments, an approach or method for producing chlorine solutions may include the following procedures.

1. Use the nominal or labeled concentration of the analyte, particularly the stock sodium hypochlorite solution, usually between 5 and 10%, and add 80% of the expected volume to 80% of the water. This water should be chlorine free and of good quality. Record the volume or weight of the additions carefully.

2. Measure the chlorine content of the resulting solution with a reference method. In this case, a reference method can be selected from among the chlorine test procedures found in Standard Methods of Water Analysis. One skilled in the art can readily back calculate to the actual concentration of the initial stock chlorine solution using volume×concentration equals volume×concentration calculations.

3. Using the calculated actual concentration, a similar direct calculation yields the additional water and chlorine stock solution that need to be added to prepare the desired amount of chlorine solution at the desired concentration.

4. This chlorine solution is metered into the polyethylene bottles. The precision of this metering directly impacts the precision of the reference fluids. In practice it has been found 100+/−0.05 mls to be achievable and suitable.

5. Five to seven days after filling, lots are testing directly for concentration and as used with pH adjusters to make reference fluids. The particular reference fluids described here lose 0.3 ppm chlorine due to bottle shock and reaction with the pH adjusters.

Given the importance of the chlorine solution to the blended reference fluids, all of the calculations and quality control data are included in a designed for purpose spreadsheet. This spreadsheet also provides information necessary for the validation process, as discussed below, including lot numbers for both pH adjuster and chlorine solutions. Lot numbers are an important tool for trace back and age control. Chlorine solutions are coded for a 4-month shelf life but appear to have more than 6-month shelf life in general storage.

Figure 3:
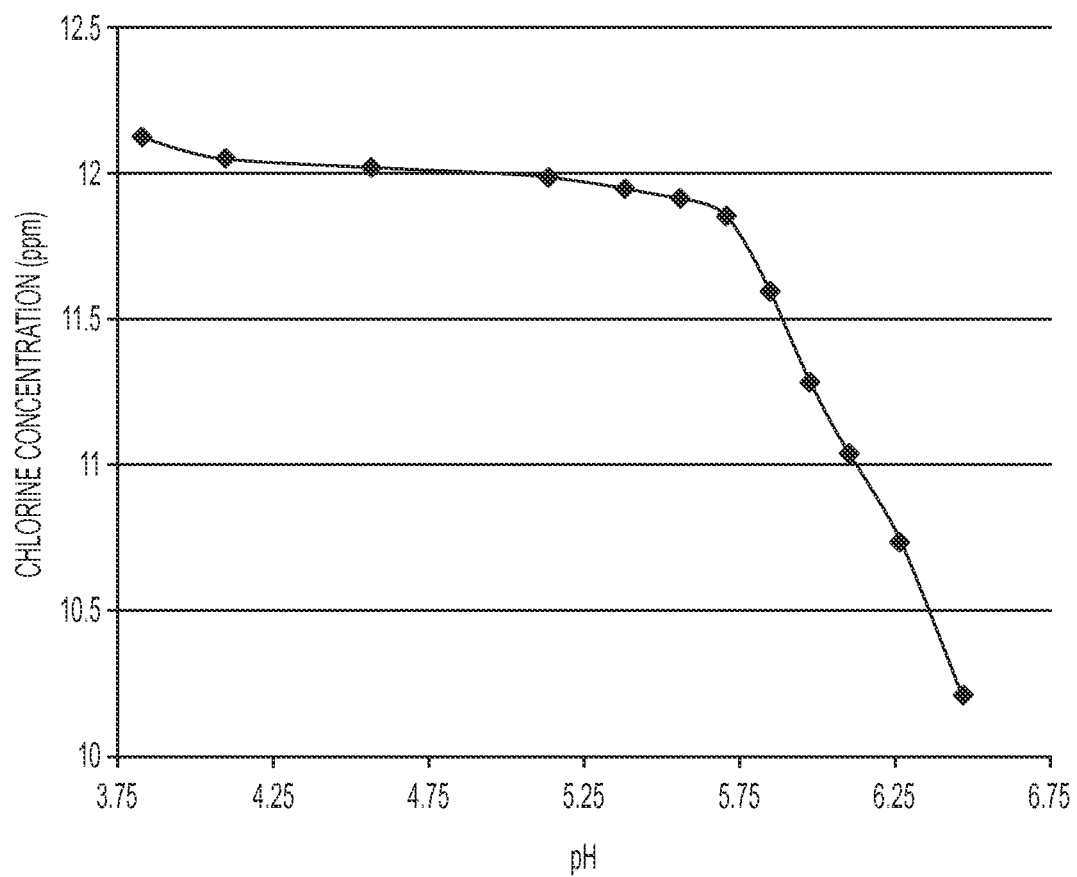
FIG. 3 is a graph showing the impact of pH on sensor response in accordance with an exemplary embodiment.

FIG. 3 illustrates the change in response due to pH change for a single solution. This change in response prompts the need to match the pH of the calibration solution to that of the process stream. If the pH is not matched, the calibration may be invalid. The pH dependence of response is driven by the equilibrium between hypochlorous acid and hypochlorite ion as a function of pH. The response to chlorine is lower at higher pH over the range of three reference fluids with various pH levels as shown in Table 1. For example, if the pH of calibration was 6.5 and the line is operating at pH 5, the probe and data reporting system would erroneously over report the chlorine level. If a line is to be operated at lower than pH 5, it would be advantageous to have additional reference fluids, but these are less critical as the effect of lower pH on probe response is small beyond pH 5 when all of the chlorine in solution is present as hypochlorous acid. However, it should be noted that chlorine outgassing becomes a potential problem at lower pH values unless mitigated with a wash adjuvant.

According to an exemplary embodiment, when calibrating a chlorine probe, a food wash reference fluid delivery apparatus, which may also be called a reference delivery system, may be manually connected to test a sensor. The flow is adjusted to match the flow when the process stream is being tested, for example, at about 1 liter per minute. It is important to match the flow to the extent possible. Directly measuring the time taken to collect about a liter of material is a practical method to measure flow in the wet environment of a produce processing facility. This flow measurement may be done where the process stream flows to the floor after passing by the chlorine sensor but is not limited thereto. Further, multiple reference delivery systems may be available and may be designed for the wash down environment of the plant. They could be plugged into each of the lines and therefore shifting from one line to the next would not be needed. On the other hand, in a single moving system, there may be advantages to moving the equipment to the lines as needed, for example, only one reference fluid needs to be prepared, and upkeep and maintenance is lower.

Once the reference fluid is flowing at the proper flow rate, it is appropriate to monitor the probe output while multiple observations are made. The values are used to calibrate the probe. This calibration can be done with either software control or by manually adjusting the offset for the chlorine probe signal processes. For validation, the probe is monitored for an additional time to assure that the system is properly reading the correct value. These operations can be done under automated control if the capital costs are justified.

Once the basic calibration of the water monitoring sensors is complete, the verification process needs to be considered. This may be a more complicated process with many branches in the logic. The first procedure to making a decision is understanding the processing objective. In the illustrative produce processing operation, the goal is to process within the domain of the FDA Food Safety Modernization Act (FSMA) validated process when such a process is provided. However, since currently no validated processes for produce is provided the goal is to process produce using a validating process that is in line with, or can be adjusted to meet, a set validated process. For this discussion on an exemplary embodiment, select ranges for the three sensor monitored parameters are selected to illustrate one such validating process. These parameters have operating ranges and limits of acceptability beyond which product should not be sold as being potentially unsafe or damaged. For this discussion of one or more exemplary embodiments, pH 5, 15 ppm chlorine, and 34 degrees F. have been identified as the set points. These points are nominally the center points of the operational range. However, in this system the measurements are not of equal importance, and the measurements have interdependence as previously discussed.

Given the interdependence of the three measurements, the valid range for all combinations of these three measurements must be valid. For example, if pH is lower, the observed chlorine level is higher than is present in the solution. This can be exacerbated if the temperature is also on the high end of the range. This knowledge is specific to any process and is necessary to confirm that a process is operating properly. In accordance with one or more exemplary embodiments, the focus is to ensure that the measurements themselves are sufficiently accurate to confirm that the process is valid.

In accordance with one or more exemplary embodiments, a process range for temperature is 32 to 40 degrees F. A chlorine range is 8 to 20 ppm, and finally the pH is 4.8 to 5.26. It should be noted that the ranges are not symmetrical around the set points due to process factors such as the undesirable effects of freezing the fresh product and the lower sensitivity to pH change around pH 5. These ranges become the process limits and are determined by where the combination of all the parameters yield undesirable outcomes. These ranges are important because they determine the specific precision of the measurements and particular accuracy of the calibration. Also, coping with both measurement variance and process variance is also implemented because if either of these variances are too large, the process is incapable of achieving the desired process.

According to an exemplary embodiment, in practice, processing lines are capable and can deliver controlled processes using the system. The balance of this discussion will focus on the validation of the calibration and measurement process. This is a process that relies on a collection of measurements, which may also be called historical data from previous calibrations. Each cycle should occur frequently enough so there is confidence that everything in between cycles of review is expected to be within tolerances. Tolerances should be statistical in nature as there is often error in any single trial. In fact there may be error associated with the reference fluids that are used to start this process. These starting errors are the key to the validation process. No amount of effort is likely to make the process measurements more accurate than the reference fluids.

By way of example, and in accordance with an exemplary embodiment, an initial error as measured by standard deviation in a temperature measurement will be between plus or minus 0.2 and 0.5 degrees depending on the accuracy of a reference thermometer. For pH, the value will be between 0.1 to 0.3 pH units. For chlorine, the accuracy of the described reference is 0.2 ppm. With these ranges, no calibration is needed when a t-test (two-tailed with different variances) does not show even a directional difference between the observed or reported measurement by the sensor. Normally a significance level of >20% is useful for this purpose. To stay in this range, a calibration may be done when there is a 10% confidence (possibly directional) that there is a real difference between the readings and the standard. If the difference becomes statistically significant (<5%), the measurements since the last calibrations need to be examined in the light of the required adjustment to ensure that the process was within the validated region.

These calculations may be somewhat onerous to calculate but can be easily automated with the t-test function of a spreadsheet or with for-purpose coding that is either local or central. It has been useful to group data from multiple lines and plants with data transfer links to assure that deviations are detected rapidly and addressed.

An important element to this validation process is the accumulation of calibration history. This data provides a lens for determining the significance of the observed process variance. This process allows establishment of the periodicity of this confirmation process. The cost of deviation from control and the magnitude of an allowed deviation allow direct determination of how this validation process should be managed. In practice, systems have been shown to remain in calibration when process parameters are held constant for several weeks.

As discussed above in the exemplary embodiments, specific formulations were provided for three different reference fluids for calibrating chlorine sensors as shown in Table 1 of FIG. 2. In accordance with one or more exemplary embodiments, these materials may be tailored for this specific purpose and reflect knowledge of the chemistry of the chlorine sensors. This tailoring process is generally applicable to sensor calibration and validation. To illustrate this process, four aspects are considered here. These aspects include reference methodologies for determining concentration of the analyte such as chlorine, identifying the controlling variables for sensor response, selection of materials for stability and accuracy, and the extension to references beyond chlorine.

Figure 4:
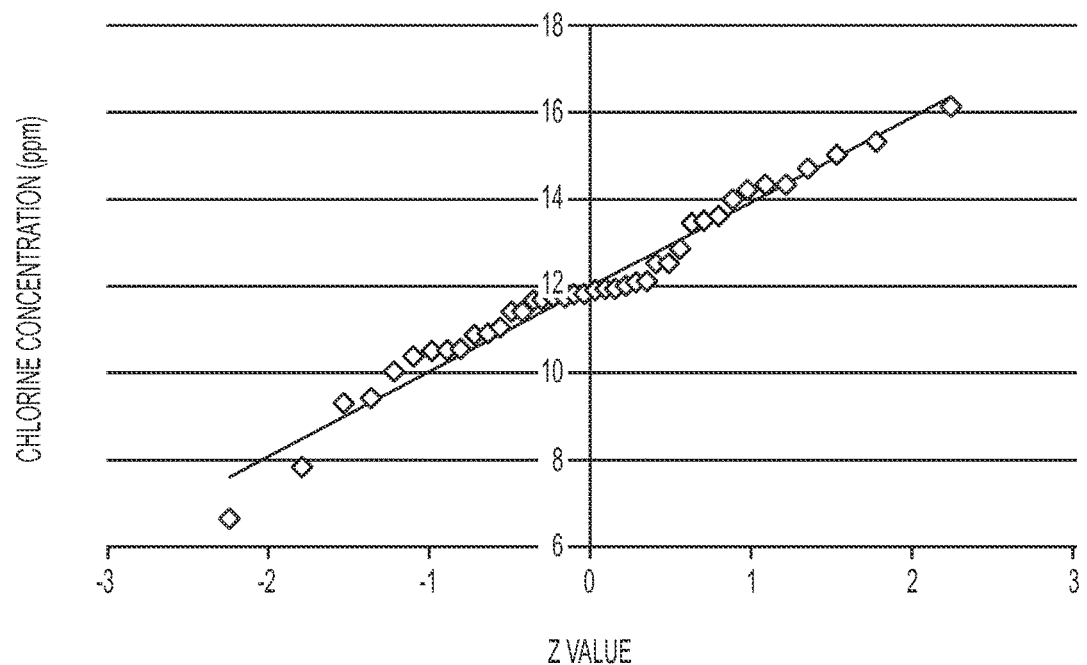
FIG. 4 is a graph showing a normal probability plot for colorimetric chlorine determinations in accordance with an exemplary embodiment.

FIG. 4 illustrates the random or normally distributed nature of the error in 40 of 45 chlorine determinations by 15 different individuals using commercial test kits. Five results were rejected as outliers in this total data set. From this graph, one can determine that the mean of this data is 12 ppm with a standard deviation of 2 ppm.

The reference method used to prepare, or at least audit the preparation of reference fluids, should provide precision and accuracy. In the case of chlorine measurement, there are numerous candidate procedures. Further, for a clean water system with pH control, total and free chlorine are essentially the same because there are no organic materials to combine with the chlorine. The desire to use commercial procedures or widely accepted procedures such as the tablet or powdered based test kits should be resisted. As illustrated by a normal probability plot shown in FIG. 4, these procedures lack the precision necessary and would introduce an overwhelming amount of error into the calibration and validation process. For example, for a single solution, 15 operators determined that the chlorine concentration with 12+/−2 ppm when the solution was known to be 12.6+/−0.2 ppm by a reference method. This tenfold difference in error is easily the difference between control and out of control for a process. A simple well known thiosulfate titration method has proved useful as a reference method. The results for this method appear to be independent of the factors discussed in the next section allowing for the preparation and audit of multiple reference fluids.

Temperature and pH are known to affect galvanic sensor response. The effect of pH was previously illustrated in FIG. 3. As shown in that exemplary embodiment, a calibration at pH 6.5 will not apply at pH 5 and vice versa. Temperature is a secondary factor in the case of the chlorine sensor but is much more important to pH where temperature compensation is intrinsic to the module converting potential to pH. The illustrated shift in response prompted development of the three reference fluids, described in Table 1 of FIG. 2. which yield specific pH values which are used when processing.

For other systems, different and/or additional factors might control sensor response and therefore need to be controlled in reference fluids. A short list of candidate factors include ionic strength, viscosity, sequestering agents, and interferences. When designing the reference fluid, it is important to focus on the agent to be measured and what factors will interfere with generating the true response.

Considering the selection of materials of standards, stability, and suitability are important. In the case of chlorine where pH needed to be controlled, the standards eventually developed as a two component system with a pH adjusting component and a source of chlorine. For the pH adjusting portion, many different buffer systems could be considered including but not restricted to carbonate, organic acids, and phosphate systems. In this particular instance a phosphate system was selected as it is the buffer system used in the process line and so would be least likely to interfere with the readings. With regards to the chlorine source, sodium hypochlorite was ultimately selected even though it would entail shipping a small bottle of liquid. Calcium hypochlorite was investigated as a dry alternative but commercial preparations are too granular and too inhomogeneous to provide the needed consistency. In addition, calcium hypochlorite slowly gives off gaseous chlorine which limits the storage life of the reference fluids.

According to one or more exemplary embodiments, when calibrating any sensor, many principles may apply that are also later used for validation. Sometimes a reference method is trivial as for temperature where a physical property is measured. In other cases it can be complicated such as for conductivity where fouling and temperature can be very important. It is important to test the applicability of the method and develop a statistical picture of its performance. The calibrated sensor will only approach the accuracy of the reference method. Controlling factors and interferences are intrinsic to the sensor choice and process stream. Appropriate references allow the sensor to correctly see through this haze. This view will be enhanced with an understanding of the actual attribute to which the sensor responds. For example, a membrane based dissolved oxygen sensor actually measures the chemical potential of the oxygen and not the specific concentration. Therefore, a reference should have the same saturation curve as the process stream for useful determination. For chlorine dioxide and other oxidizing sanitizers the process is more similar. Ultimately, useful calibration and validation is a recursive process that continuously builds on prior history.

According to an exemplary embodiment, calibration and verification of a sensor, which may include electrodes, is done to ensure a system, and associated equipment, is accurately measuring a process wash fluid pH and free chlorine (as hypochlorous acid) within an acceptable range and thus injecting a required amounts of washing agents such as chlorine. The data generated provides a base line and historical background on the system performance such as measurement consistency of the pH and CI sensors, errors, and drifts. The data records provided by routine calibration and verification are used in the validation of the process wash water food safety program. The overall chlorine sensor calibration operating procedure consists of preparing a chlorine solution for chlorine sensor that may include chlorine electrodes, assembling a calibrator unit used to perform calibrations and verifications, and performing the calibration and verification of the sensors that include chlorine electrodes.

Calibration and verification of the chlorine electrodes may be performed using a chlorine calibration/verification kit for creating the chlorine solution, which may also be called the reference fluid, and using a calibrator unit, which may also be called a food wash reference fluid delivery apparatus. The chlorine solution to be used in the calibration and verification of the chlorine electrodes is prepared using the chlorine calibration/verification kit consisting of a pH adjuster and a chlorine calibration standard. The pH adjuster and chlorine calibration standard are an acid and a base, respectively. Thus, the pH adjuster and chlorine calibration standard should be treated with care and not brought into contact while in their concentrated forms. The pH adjuster and chlorine calibration standard should be diluted prior to mixing.

The chlorine calibration/verification kit may consist of a chlorine calibration standard and a pH adjuster that are designed to meet produce wash lines operating pH targets. For example the pH adjuster may have a set point pH of 5.5 or lower, a set point pH of 6.0, or set point pH 6.5 depending on the produce wash line target operating pH which may be dependent on, for example, the specific produce being washed in the line.

According to an exemplary embodiment, a chlorine calibration/verification kit may be composed of eight pH adjusters for a specific pH point and eight chlorine calibration standard bottles. Each kit will also have a reference that will provide information on the expected chlorine concentration and standard deviation of the chlorine standard. The expected chlorine concentration is based upon the final chlorine standard solution in the reference fluid.

According to a specific exemplary embodiment, a chlorine standard solution, also called a reference fluid, may be preparing using a 30 kilos scale that has a precision minimum of two significant figures, for example, 0.01 kg, 18 kg of distilled or better grade water, one carboy with lid, a calibrator unit, a colorimeter, a chlorometer, a turbimeter, distilled water, adjustable pipettes, a hand held pH meter, a buffer solutions: 4.0 and 7.0, one liter plastic bottle, plastic beakers, and gloves. According to another exemplary embodiment, the chlorine standard solution or reference fluid may be prepared using a subset of these items or additional items not listed above.

According to an exemplary embodiment, a procedure for preparing a chlorine standard solution includes selecting a pH adjuster level required for an electrode to be calibrated/verified. Next the procedure, or method, includes carefully opening the selected pH adjuster packet, removing all the pH adjuster from the packet, and transferring the pH adjuster to a clean one liter plastic bottle using distilled water to rinse the packet. Then distilled water is added to the plastic bottle, the bottle's cap is tightened and the bottle is vigorously shaken until all the pH adjuster is completed dissolved, and then sufficient water is added to fill the bottle.

Figure 5:
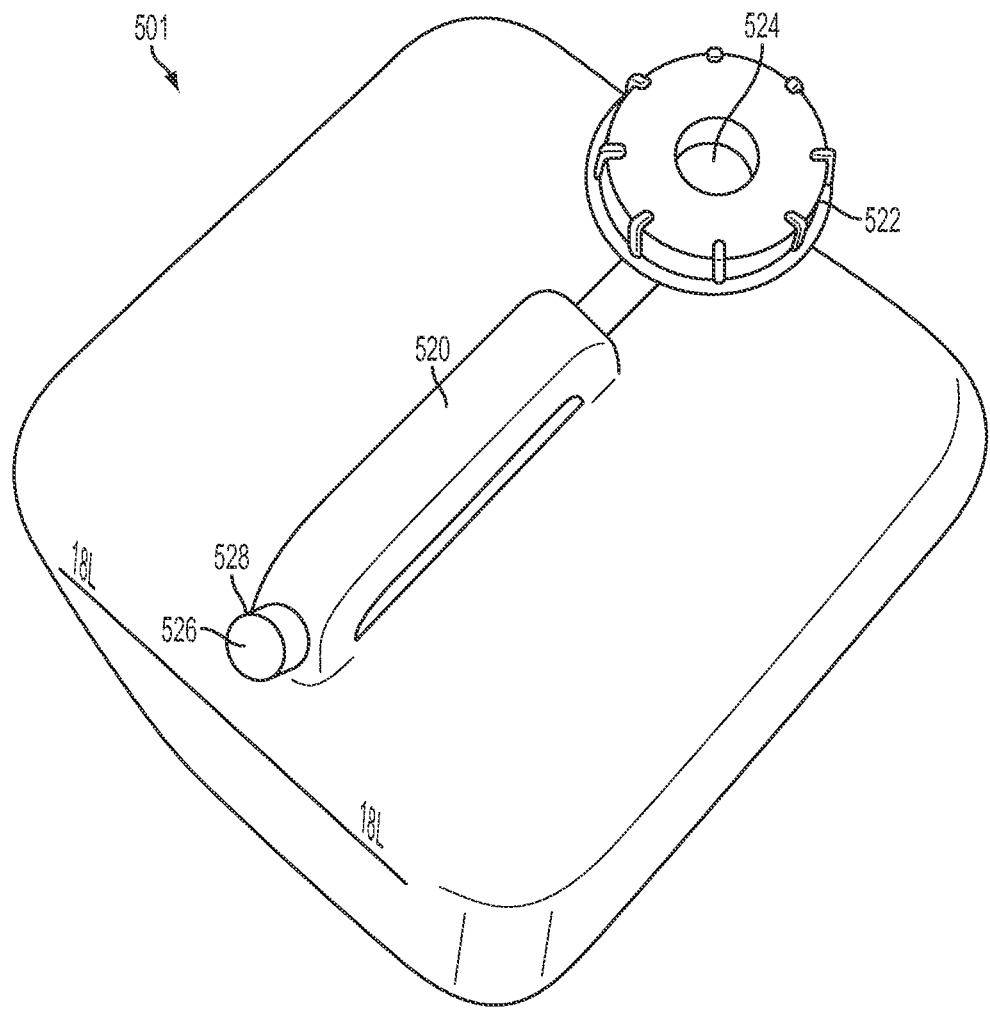
FIG. 5 is a carboy in accordance with an exemplary embodiment.
Figure 6:
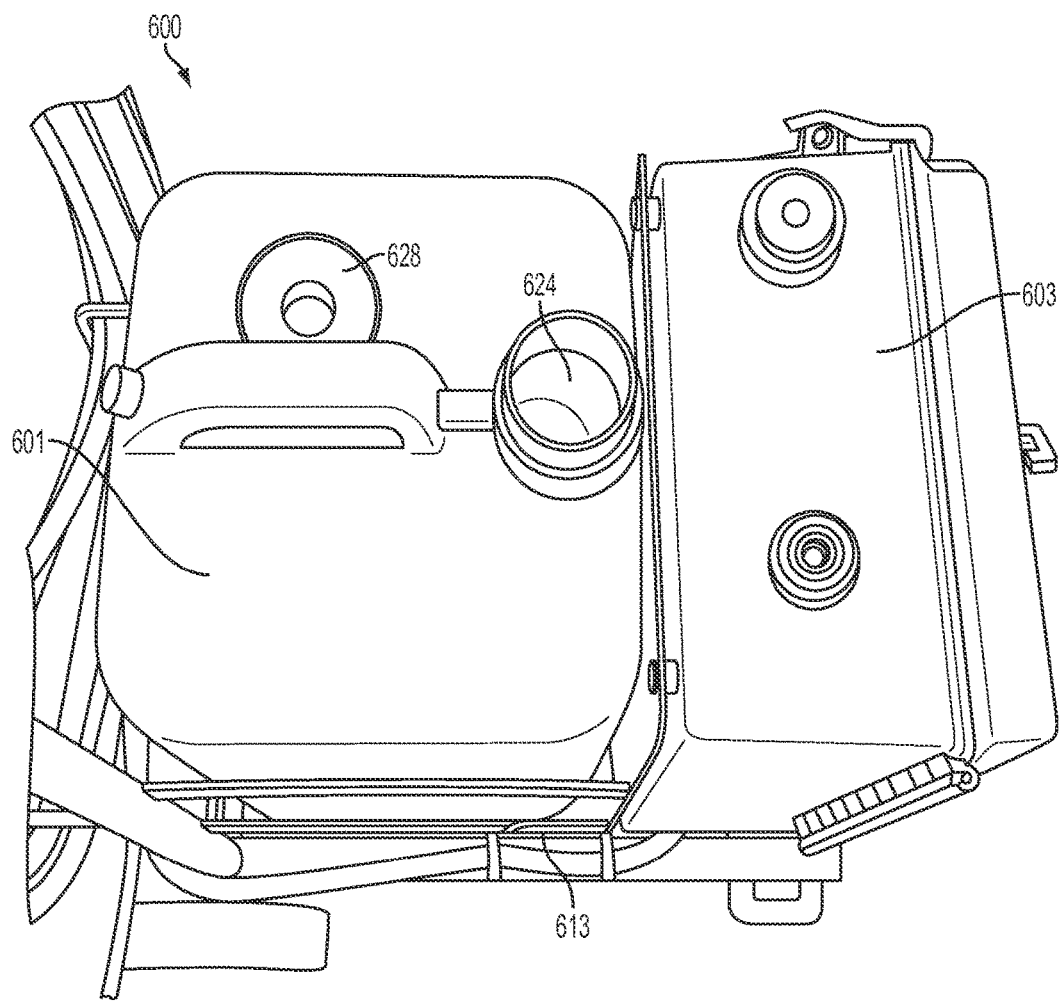
FIG. 6 is a carboy and pump placed on a frame of which make up a calibrator unit in accordance with an exemplary embodiment.

Next, the chlorine standard solution is moved and prepared in a carboy which serves as a reference fluid reservoir. An example of a carboy (501), which may also be called a reference fluid reservoir, is shown in FIG. 5. The carboy (501) has a lid (522) that covers the main opening (524) as well as an airlock (526) with a lid (528) covering that opening. The carboy may also have a handle (520). Specifically, a clean and empty carboy (601) that comes as part of the calibrator unit (600) may be used, as shown in FIG. 6. The calibrator unit (600) may also be a called a food wash reference fluid delivery apparatus. The calibrator unit (600) also includes a pump (603). Then the carboy (601) is weighed to acquire the tare weight using a scale that can measure to at least 30 kg. Once the scale is tared, approximately 6 kg of distilled water is added to the carboy (601) through the main opening (624). The pH adjuster solution prepared in a one liter bottle and is carefully added to the carboy (601) containing the 6 liters of distilled water. If undissolved pH adjuster is transferred to the carboy (601), the carboy (601) will need to be shaken or stirred until the pH adjuster is fully dissolved. Then the pH adjuster bottle is rinsed with distilled water, and the rinse is added to the carboy (601) along with another 3 kg of distilled water. The lid (628) is placed on the carboy (601) and tightened to it firmly, and then the carboy (601) is agitated mixing the solution well.

Next the chlorine calibration standard is added to the carboy (601). The lid (628) is placed on the main opening (624) of the carboy (601) and tightened firmly, and again the carboy (601) is agitated to mix the solution well. The small chlorine calibration standard bottle is then rinsed twice, and the rinse is added to the carboy (601) both times.

Further, the carboy (601) is filled with distilled water till the tared carboy weighs 18 kg. Then the lid (628) is placed on the carboy (601), it is tightened securely, and then the carboy (601) is agitated to mix the newly prepared chlorine standard solution which is also called the reference fluid, and the complete carboy (601) is placed on the calibrator carboy storage compartment (613) of the calibrator unit (600).

Figure 7A:
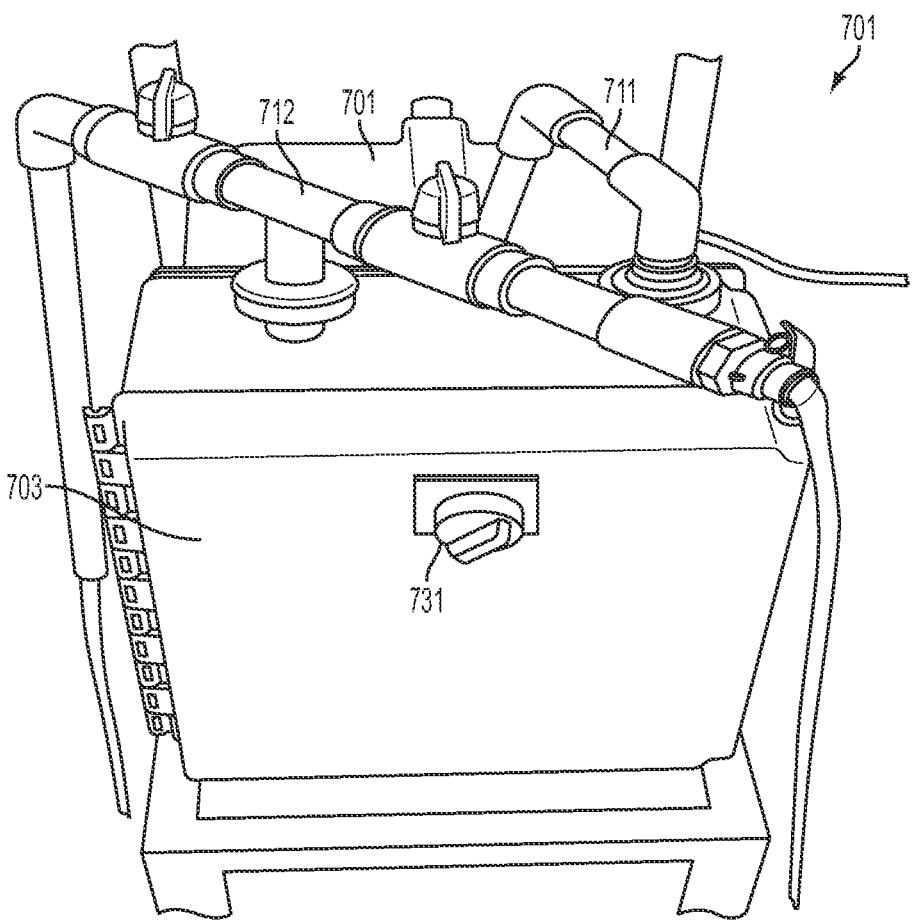
FIGS. 7A and 7B show inlet and outlet pipes in the assembled calibrator that are connected and arranged in a self-priming mode, and a view of the control switch in accordance with one or more exemplary embodiments.
Figure 7B:
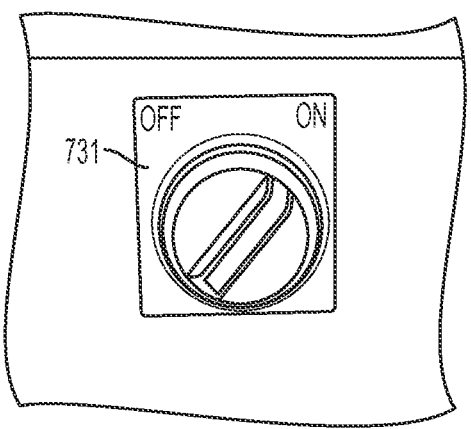

As shown in FIGS. 7A and 7B, the inlet pipe (711) and outlet pipe (712) in an assembled calibrator (701), which is also called a food wash reference fluid delivery apparatus, are connected and arranged in a self-priming mode such that when the calibrator pump (703) is turned on using the control switch (731) for a few seconds so that any water retained in the pipes (711, 712) and pump (703) from previous runs is discharged. The inlet and outlet pipes (711, 712) are then connected and arranged in a recirculation mode such that the chlorine standard solution within the carboy (701) is recirculated for a minute or two. Once the chlorine calibration solution has been thoroughly mixed the solution will have the listed level of free chlorine which may be confirmed using a quality assurance process. In one embodiment, when self-manufacturing chlorine standards, an extensive quality assurance program may be implemented to assure the accuracy of the chlorine standard solution.

According to an exemplary embodiment, data generated during preparation of a chlorine standard calibration solution, which is also called a reference fluid, may be evaluated in order to make sure that correct standards have been prepared in a correct manner for the verification and calibration of specific chlorine electrodes based on their pH set point requirements. For example, three chlorine standard solution samples taken from a carboy may have similar free chlorine values (within 0.5 ppm) when analyzed by a reference method. The average free chlorine value of the three chlorine standard solution samples should be no more than ±0.5 ppm different than the chlorine standard solution value as stated in the reference information included in a chlorine calibration/verification kit that may be used. Additionally, the three chlorine standard solution samples should have similar pH values (within 0.3 pH points). The average pH of the three chlorine standard solution samples should be no more than ±0.3 pH points different from the pH value stated in the pH adjuster used to create the reference fluid chlorine standard solution. Once a review of the data indicates that all the values generated during the preparation of the chlorine standard solution meet expectations, then proceeding with the calibration/verification of the chlorine electrodes may take place.

However, according to another exemplary embodiment, if review of the data indicates that the values generated during the preparation of the chlorine standard solution do not meet expectations, a review of certain items may be executed to diagnose and fix the discrepancy, particularly making sure all equipment such as pipettes, pH meters, chlorine assay, and scales are functioning correctly and have been calibrated. A review of the testing devices and the testing skills of the technician may also be reviewed. For example, a technician should be able to measure free chlorine levels in distilled water both accurately and precisely. Chlorine measurements in distilled water should have standard errors of <0.1 ppm when done by a single technician with a single instrument or other reference method. The chlorine standard solution may be retested by taking three additional consecutive samples after the solution has been re-mixed for an additional 2 min. If the measurement results still do not meet expectations, a new chlorine standard calibration solution may need to be prepared with a new chlorine calibration standard. Alternatively, it can be appreciated that a senior and/or highly skilled technician could adjust the contents based on the measurements to get the solution to meet expectations.

Figure 8A:
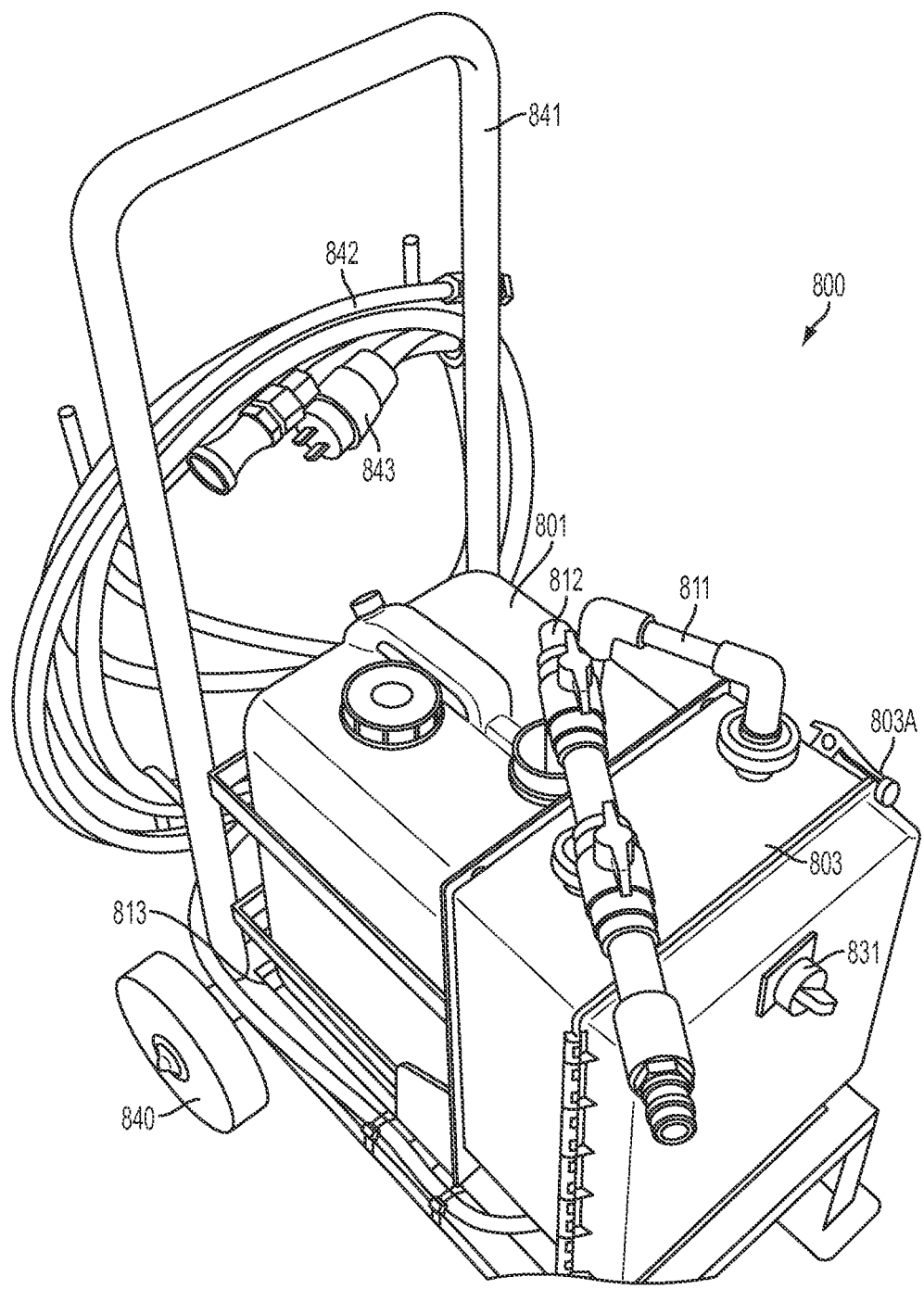
FIGS. 8A and 8B are views of a calibrator with and without a carboy and piping in place in accordance with one or more exemplary embodiments.

According to an exemplary embodiment, as shown in FIG. 8A, a calibrator (800), also called a food wash reference fluid delivery apparatus, is a unique tool/vehicle developed as a means to deliver a chlorine standard solution, also called reference fluid, to a chlorine electrode used in a produce wash line in order to calibrate and verify the chlorine electrode sensor. The calibrator (800) may include a wheeled (840) metal frame (841), a two gallons per minute (GPM) pump (803) housed in a fiberglass case (803A), a carboy (801), a hose with pump connections (842), and a power cord (843). The calibrator (801) will allow a user to match the operational flow rate in the fluid flow path of the wash water across the chlorine electrode during both calibration and verification activities, thus meeting a requirement for the accurate measurement of chlorine levels.

Figure 8B:
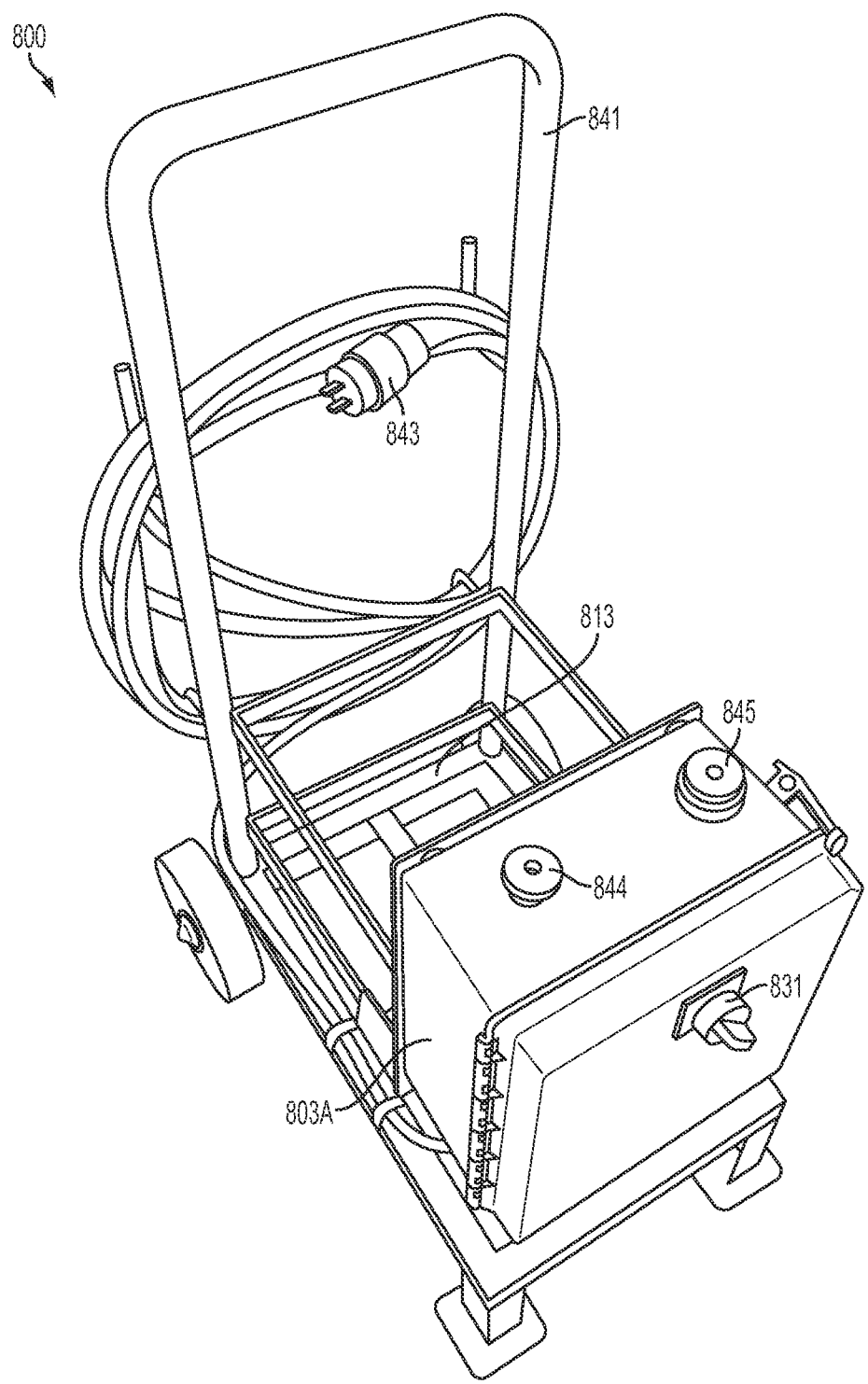

According to an exemplary embodiment, as shown in FIG. 8B, a calibrator (800) may include a 25 foot power cord (843), a pump in a pump housing (803A) that includes a male outlet port (844), a female inlet connection (845), an on/off switch (831), and a carboy storage area (813) which are all mounted together on a mobile frame (841).

Figure 9A:
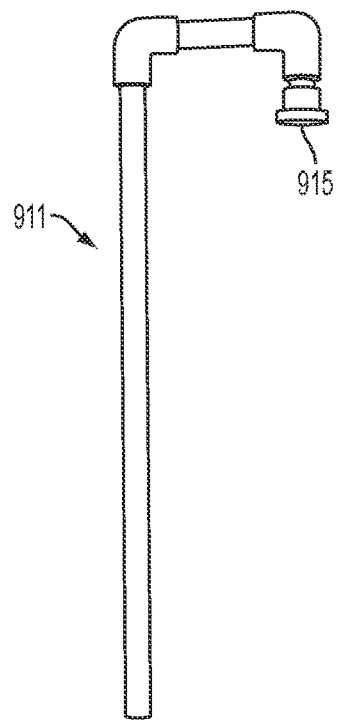
FIGS. 9A, 9B, 9C, and 9D are views of an inlet pipe, an outlet pipe, a carboy, and a tubing connection, respectively, in accordance with one or more exemplary embodiments.
Figure 9B:
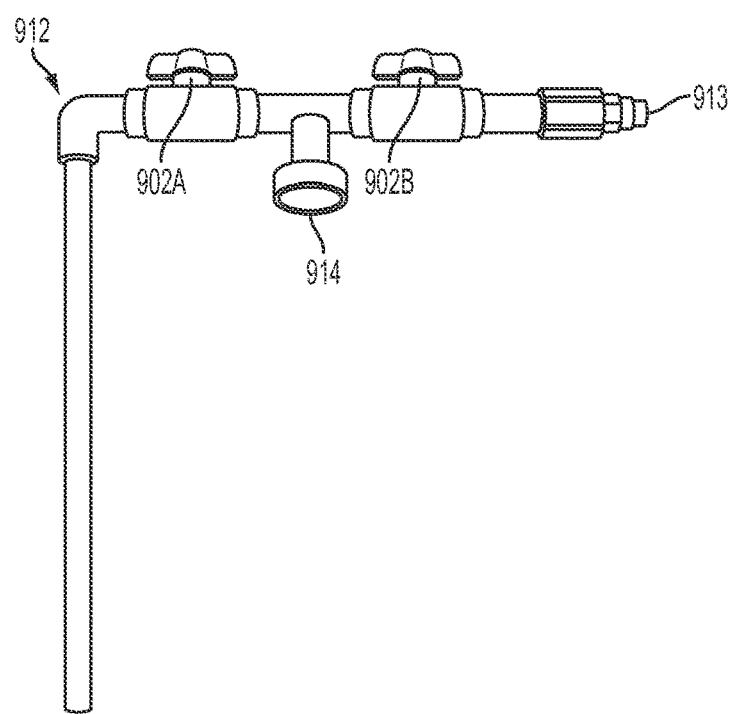
Figure 9C:
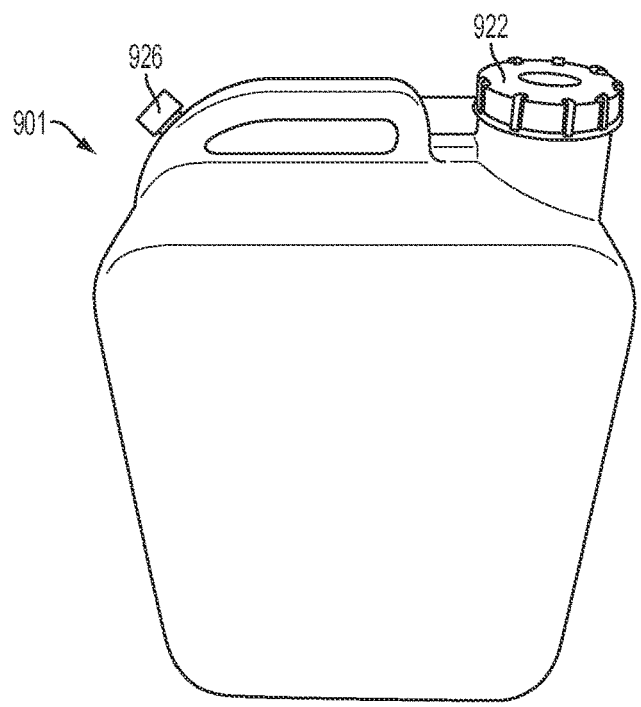
Figure 9D:
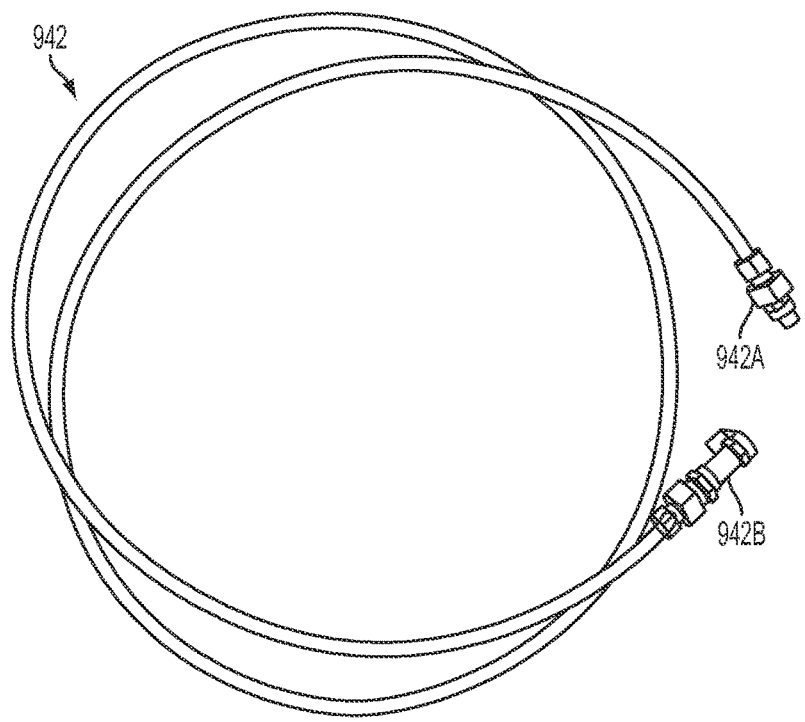

Further, according to one or more exemplary embodiments, a calibrator may include an inlet pipe (911) with a male connector (915), as shown in FIG. 9A, which is used to carry chlorine solution from a carboy into a pump. The calibrator may also include an outlet pipe (912) that has a set of control valves 902A and 902B, a female connector (914), and an output male connector (913), as shown in FIG. 9B, which is used to connect and control the flow of the reference fluid chlorine solution going into the chlorine sensor located along the fluid flow path of a process stream. A carboy (901), as more specifically shown in FIG. 9C, may include a lid (922) and an airlock (926) and may be used to mix and store the reference fluid chlorine standard solution for calibration and verification of the chlorine electrodes. It can be appreciated that the capacity and shape may vary. A food wash reference fluid delivery apparatus, or calibrator, may also include a tubing connection (942), as shown in FIG. 9D, which may specifically be a ⅜" connection tube with a 5/16" male jaco connection (942A) and a female quick connect (942B) and may be used to connect the calibrator unit to flow cells leading to a fluid flow path along a produce process stream along with a chlorine electrode sensor to be calibrated and verified is located.

Figure 10A:
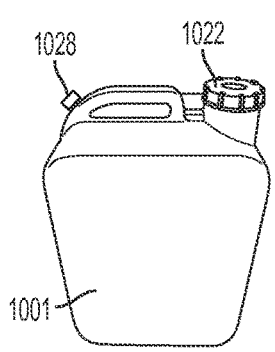
FIGS. 10A, 10B, and 10C show a carboy being opened and placed into the calibrator in accordance with one or more exemplary embodiments.
Figure 10B:
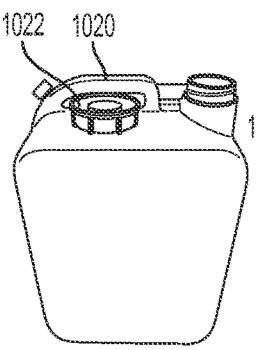
Figure 10C:
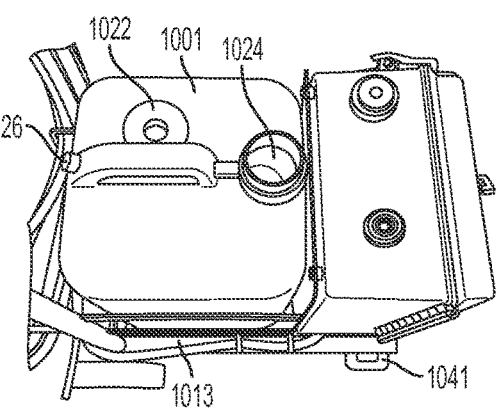

According to an exemplary embodiment, a calibrator may be assembled as follows: Initially a lid (1022) of a carboy (1001) that contains the reference fluid should be removed and then the carboy (1001) should be placed onto the cart (1041) in the designated carboy storage area (1013) as shown in FIGS. 10A-10C. It is recommended that a lid (1028) for the airlock (1026) and the lid (1022) for the main opening (1024) of the carboy (1001) be placed under the handle (1020) of the carboy (1001).

Figure 11A:
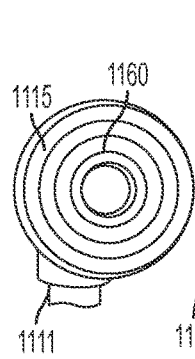
FIGS. 11A, 11B, 11C, and 11D, show an inlet pipe arranged and connected as part of a calibrator in accordance with one or more exemplary embodiments.
Figure 11B:
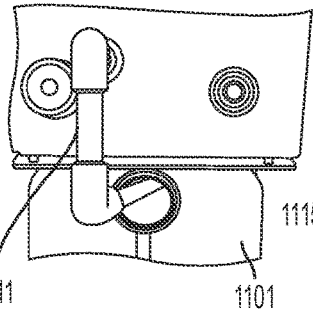
Figure 11C:
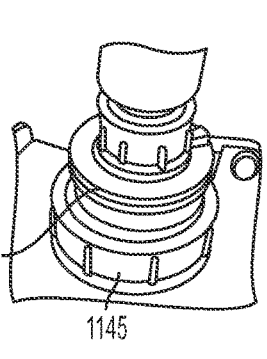
Figure 11D:
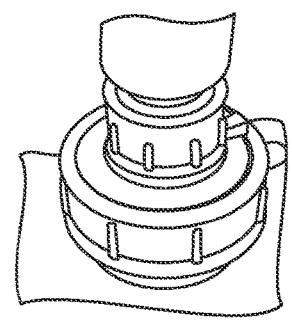

Next the inlet pipe (911), as shown in FIG. 9A, is connected to a pump and carboy. Specifically, in accordance with an exemplary embodiment, one may verify that an O-ring seal (1160) is on a male connection (1115) of an inlet pipe (1111), as shown in FIG. 11A. If it does not have one, a new seal should be inserted. One may then inset the longer side of the inlet pipe into a carboy (1101) as shown in FIG. 11B. Then one may line up the inlet pipe male connection (1115) to a female inlet connection (1145) on a pump housing, as shown in FIG. 11C, and then tighten the parts together turning counter-clockwise, as shown in FIG. 11D.

Next, the pump may be flushed. Particularly, one may line up the female connection (1214) on the outlet pipe (1212) with the male outlet port (1244) on the pump housing, as shown in FIG. 12A, arranging the side without the valves (1261) outside of the carboy, as shown in FIG. 12B, and then tighten the two pieces together, as shown in FIG. 12C. Then one may turn both ball valves on outlet pipe to 45 degrees open, as shown in FIG. 12D. One may then plug in the power cable into an outlet using, if possible, a water protected outlet. Then one may turn on the calibrator for about ten seconds letting water run to the ground, as shown in FIGS. 12E and 12F. This will flush the pump of any previous solution that may reside in the pump and tubing.

Figure 13A:
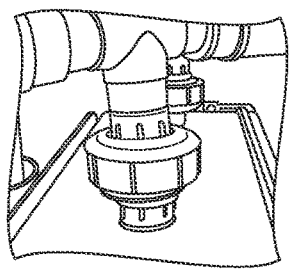
FIGS. 13A, 13B, and 13C show an inlet pipe being arranged and connected as part of a calibrator in accordance with one or more exemplary embodiments.
Figure 13B:
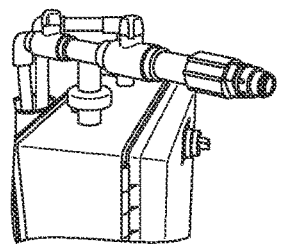
Figure 13C:
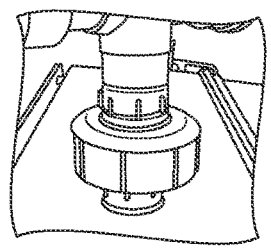

The outlet pipe may then be connected. Particularly, one may unscrew the outlet pipe from the male outlet port, as shown in FIG. 13A, and insert the end of the outlet pipe that has no valves attached into the carboy, as shown in FIG. 13B, followed by securing the female connection on the outlet pipe to the male outlet port on the pump housing as shown in FIG. 13C, by screwing the outlet pipe to the male outlet port.

Figure 14:
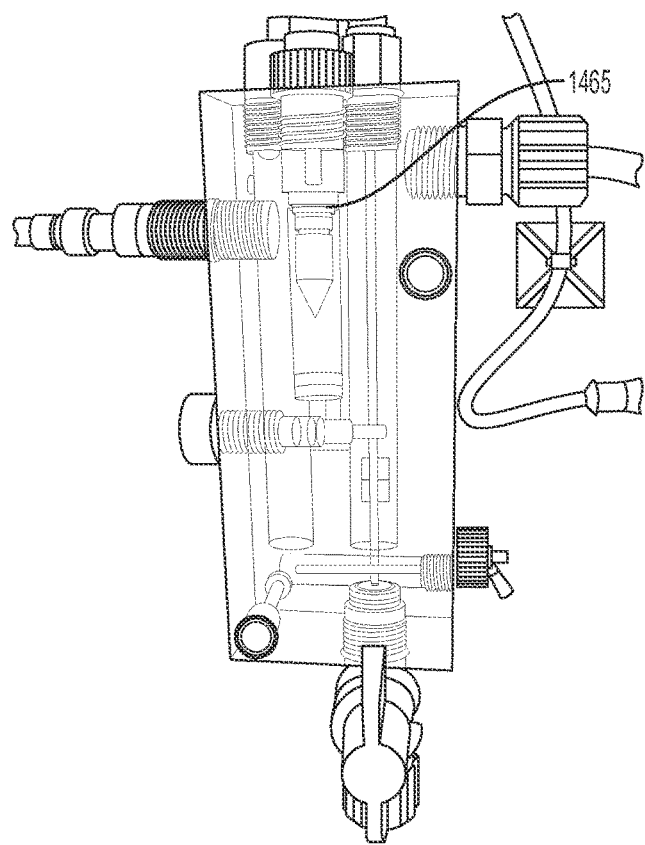
FIG. 14 is a flow cell containing a sensor in accordance with an exemplary embodiment.

According to an exemplary embodiment, the flow rate may be determined in a flow cell within which an electrode sensor is located. Specifically, before connecting a calibrator to the flow cell, one may observe and mark the operational flow level (where a float (1465) is during operations), as shown in FIG. 14. This will be used to match the calibrator flow to the operational flow. The operational flow rate as well as the calibration/verification flow rates may be in L/min.

Figure 15A:
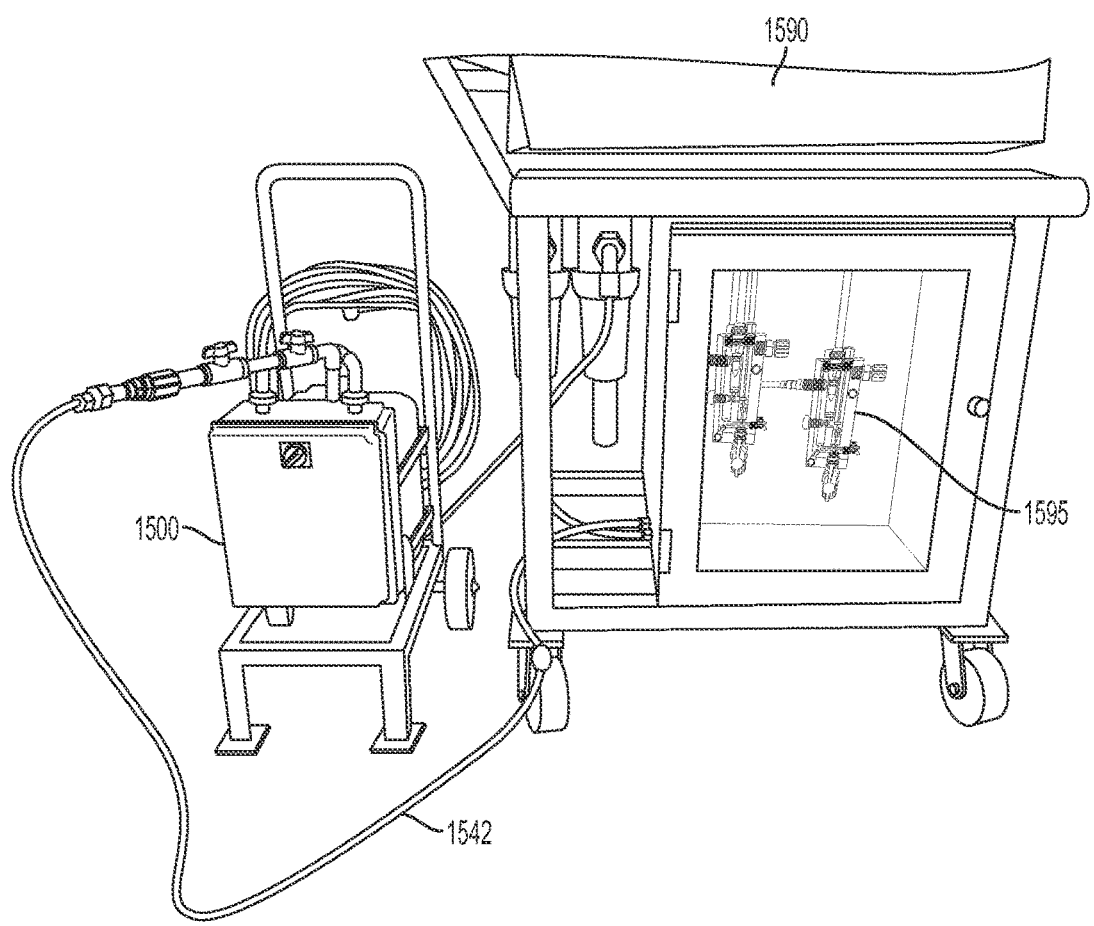
FIGS. 15A and 15B show a calibrator connected to a produce wash line in accordance with one or more exemplary embodiments.
Figure 15B:
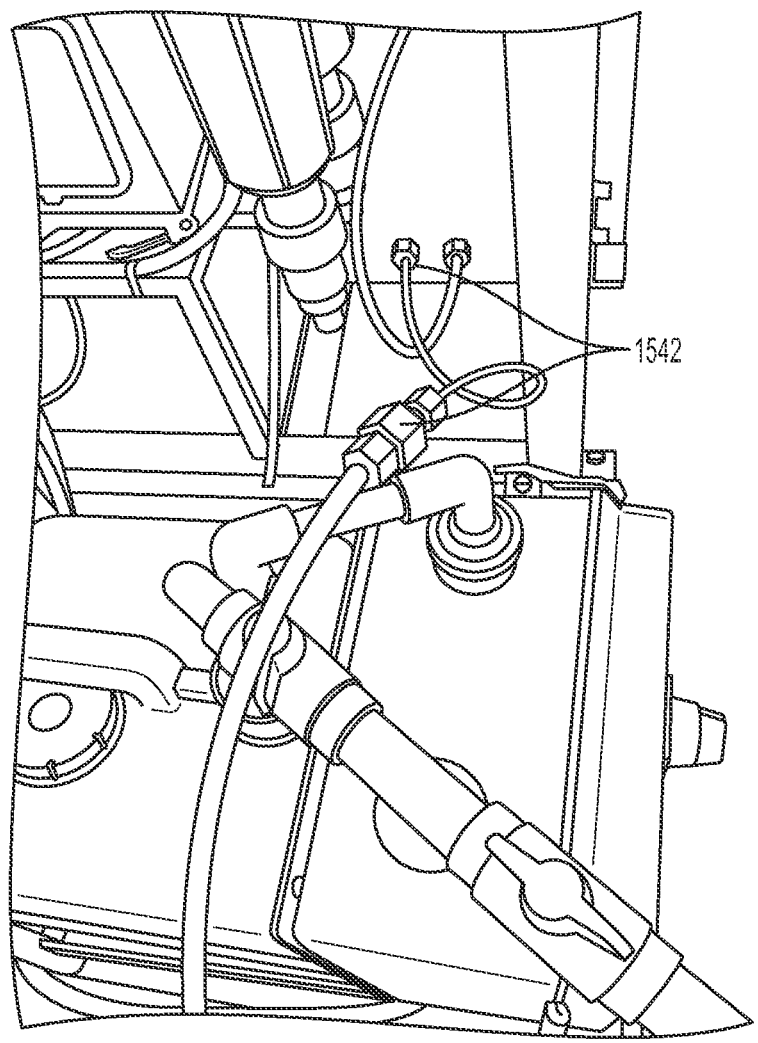

Next, the food wash reference fluid delivery apparatus, also called the calibrator (1500), may be connected to the fluid flow path of the produce wash line (1590). Particularly, the tubing connection (1542), as shown in FIG. 9D, may be used to connect the calibrator (1500) to the produce wash line (1590), where the chlorine electrode sensor (1595) is located, as shown in FIGS. 15A and 15B. Once connected, one may then turn on the calibrator pump and adjust the flow rate to the previously measured operational flow rate through the chlorine electrode sensor (1595).

Routine calibration and verification of the food wash sensor system's chlorine sensors placed along the fluid flow path of the process stream is implemented to ensure the system/equipment is accurately measuring the process wash water pH and free chlorine (as hypochlorous acid) and thus injecting the required amounts of wash solution and chlorine. The data/records provided by routine calibration and verification are used in the validation of the plant's process wash water food safety program.

According to an exemplary embodiment, at least a weekly calibration and verification of each food wash sensor system sensor is recommended. Alternatively, a food processing plant may determine and monitor the calibration frequency of each sensor based on the calibration historical trends, food safety requirements, and risk tolerance.

According to an exemplary embodiment, calibrating chlorine sensors in a fluid flow path of a produce wash unit is done to properly control an amount of free chlorine in produce wash systems. The chlorine as well as pH sensors in the produce line units may be calibrated prior to their activation. Chlorine and pH are interdependent, so both systems should be monitored and calibrated. Verification of calibration status and calibration should be performed on a regular basis. Records of calibration readings, monitoring, and any pertinent changes are preserved and used when validating the system.

Further calibration should be performed in the following specific scenarios. According to one exemplary embodiment, calibration should be performed after initial installation and prior to the produce wash line unit assuming control of the free chlorine injection and monitoring. Each produce wash line unit may be equipped with two chlorine sensors that can service two individual wash water tanks. Each of these sensors electrodes must be calibrated prior to the produce wash line unit activation.

According to another exemplary embodiment, calibration should be performed after the replacement of chlorine electrode(s). Also, calibration should be performed if the pH set point for a given wash tank under produce wash line control is changed. For example, if the pH set point for a primary wash tank is changed from 5.5 to 4.5. Calibration should be performed if the produce wash line unit has been out of service for a significant period of time. Further, calibration should be performed if review of calibration verification records shows an increased divergence from an established calibration set point for a given chlorine electrode, if flow rates through the chlorine sensor have changed significantly, and/or if daily free chlorine checks indicates a significant divergence of the free chlorine readings from values generated from an approved independent method. Further, when in doubt if a chlorine sensor is no longer in calibration, performing a verification of calibration status prior to an actual calibration of the chlorine electrode is recommended.

According to an exemplary embodiment, a calibration procedure may be done as follows: An operator may insert a carboy containing the prepared chlorine standard solution (also called the reference fluid) into the calibrator (also called the food wash reference fluid delivery apparatus) cart making sure the main lid opening is facing the pump housing. Then the operator may assemble the calibrator connection pipes/hoses for connecting to the produce wash line unit as indicated above. Then the operator may carefully move calibrator unit to the plant floor. Then prior to connecting the calibrator unit to the produce wash line flow inlet tube leading to the chlorine electrode to be verified or calibrated, the operators may set the selected chlorine and pH electrodes (primary or secondary) to Manual Mode and cut water flow to the electrodes by closing the corresponding valve on the pH u-tube and may then set the interlock relay (0-CR/3-CR) to "ON" and then connect calibrator's 5/16 female Jaco connection to the 5/16 male connection of the chlorine cell inlet tube.

Determining the operational flow rate of the wash line loop feeding the chlorine electrode is also done. The calibrator's chlorine standard solution flow rate is set to match the operational flow rate normal for the electrode loop being tested. It is recommended to mark the flow cells to consistently match the operational flow rate for each electrode on the floor. Finally, the operator may fully open the calibrator's re-circulation ball valve and the output ball valve and may adjust the flow of the calibrator by opening or closing the re-circulation valve to match the operational flow rate of the chlorine electrode wash water loop.

According to an exemplary embodiment, for verification, an operator may proceed as follows: Once a desired flow rate has been achieved, the operator may allow a system to stabilize. After the system has stabilized, an operator may record three consecutive free chlorine readings. These readings may be taken after 20 second intervals for a total of three readings in one minute and may be done by an automated component. If an analysis of these three data points indicate the values lie within the acceptable operational range for accuracy, no calibration will be required at this point. If these three data points lie outside the acceptable operational range for accuracy, an operator may proceed to calibrate the electrode and may upload the data into a web-enabled calibration storage that is accessible through a site page. Further, more or less than three data points with different time intervals may be implemented.

According to an exemplary embodiment, for calibration, an operator may proceed as follows: Once a desired flow rate has been achieved, an operator may allow a system to stabilize. After the system has stabilized, the operator may record three consecutive free chlorine readings. The operator may take each reading after 20 second intervals for a total of three readings in one minute. If the three readings lie outside the acceptable operational range for accuracy, an operator may calibrate the electrode. Calibration of the electrode may be done by entering a chlorine calibration standard value used to prepare the chlorine standard solution through an analyzer calibration screen or may be transmitted by an automated communication method. After the chlorine calibration standard value has been entered into the analyzer, the system will adjust and then after a few seconds the system will stabilize around a new calibration value. Once the system is stable, additional consecutive free chlorine readings may be taken and recorded into the system to confirm proper calibration. The readings' data points may be entered into the web-enabled calibration storage site for analysis, and the web-enabled calibration program may then send a notification indicating if calibration has been completed successfully and is meeting desired accuracy and precision.

According to another exemplary embodiment, there may be provided a fully automated validation system that may require occasional, limited, or no human intervention. An example of an environment where such a system may be implemented would be one that has experienced any one of an increase in labor costs, declining automation costs, and/or increased desire for control. In an exemplary embodiment implementing automation throughout would leave on human intervention in the event that a need for a repair arises which falls outside of the planned preventative maintenance. Further, in an automated system replaceable modules and cassettes may be implemented for providing materials. The processes would all be the same as described above except they would be executed by automatic control. With an active preventative maintenance program, one can select a mean time to failure to reduce the requirement for human intervention. The lower limit of this intervention is the increased likelihood of failure as the complexity of the maintenance system increases and of course the capital costs associated with these systems.

Further, with the use of microfluidics, similar to the microfluidics available in soft drink dispensers delivering dozens of flavor combinations, automation of the preparation of reference fluids may be provided. The concentrated components are provided in cassettes that may be replaced robotically or by periodic maintenance. With this technology, multiple reference fluids would be available for maintaining the control system even in the face of changing control parameters. Inclusion of solvent or water purification technology may be included and would reduce the storage required for manufacturing these reference fluids. For example, membrane filters would deliver high quality water which would be suitable for the reference fluid developed for the produce washing facility. One can also foresee the use of small systems to provide a nitrogen stream from air for gas references.

Further, according to an exemplary embodiment, in addition to an automated system to prepare reference fluids on demand, automated valves to alternate between the flow of reference fluid or of was fluid in the fluid flow path of the process stream to alternate between validation and monitoring, respectively, may be implemented as well. The same automated control, for example, a programmable logic controller (PLC) or other computer can capture and process the data. Depending on the specifics of the piping, a postponement in data collection may be provided to allow the various lines to flush and allow various pumps and valves to become fully activated.

According to yet another exemplary embodiment, in addition to preparation of a reference fluid and delivery of the reference fluid to the sensors being automated, automated decision making may be provided regarding the need to calibrate and/or validate or in crisis to notify of a process deviation. These notifications can be delivered in as many ways as desired including phone, email, text, and local or remote indicators.

According to a specific exemplary embodiment, there may be at least five types of data generated as part of operating a line with a validation process. This data can be coupled with other processing data to mine information and better manage the operation. Further, there may be additional sensors and optical monitoring devices that are included in the system that will increase the information value of the data generated with this validation process such as data generated by infrared, visible, fluorescent and hyperspectral systems.

The first data type is a sensor response to a reference fluid. This data can be used to statically assert that the sensor is properly calibrated. Particularly, a comparison between the mean of the sensor readings to the statistical description of the reference fluid may be done. Given the generally higher precision of the reference fluid, the results are similar if the reference is considered a constant and a determination as to whether the difference between the sensor response and the reference is significantly different from zero is calculated. In operation one hopes that there are few observed significant differences and that they are never large enough to cause product to be produced outside of the range of a valid process. It should be noted that the process capability may exceed the requirements for a safe process. This means that a significant calibration event does not always indicate that there is a problem with recent production.

The second type of data is a collection of sensor responses to the reference fluids over repeated cycles of calibration. This data can be used to create many metrics to monitor sensor performance. This interpretation of this data is an important driver of the frequency of calibration cycles. This cycle frequency will be driven by characteristics of the process stream and sensor. For example, for washing of produce, cycle times of one to two weeks have been determined experimentally for chlorine sensors. This collection of sensor data may be analyzed for trends by, for example, looking at the magnitude of any needed adjustment or the time between adjustments. If the adjustments are consistently in one direction, a projection of a time to failure when it will no longer be possible to compensate for the drift in sensor response may be generated. If the variance in sensor response is changing, it may indicate flow variation or fouling of the sensor. Diagnosing and preventing sensor problems will be driven by this data. The analysis of this data will drive an effective preventative maintenance program.

The third type of data is related to the first. The process stream is monitored relative to the first data type. This data is the process data. It may be used to answer whether the desired process is being delivered. Given that the process may be unstable and variable, it is appropriate that any process have a statistical definition and not just be an arbitrary number. With a programmable logic controller (PLC) or other controlling device, this data can be used to control the process. The sophistication of the control logic is driven by the needed or desired performance. The use of this logic to control the addition of adjuvants is also a possibility. In the produce wash system, this logic controls the addition of an acidulant and chlorine sanitizer. Feedback loops and feed forward loops allow the system to avoid large swings in pH or chlorine concentration.

The fourth type of data is related to the second. The process stream is monitored over time. This data type can be complicated to include multiple product types. This data can be used to derive a variety of metrics for monitoring process performance. The scope of these metrics is limited only by the vision of the analyst. Looking at trends within shifts or across lines is within the scope of the data. Looking for better performance among a set of lines to identify opportunities for improvement is easily within the scope of this data. This is a "big data" opportunity where data mining can be expected to lead to innovation and process improvement.

The fifth type of data is characterized as being derivative of the other four and the other operating data. Particularly, if one couples the other four data types with parameters such as acidulant use, chlorine use, product feed rates, or product quality parameters, there are again numerous data mining operations that can be expected to lead to innovation and process improvement.

Figure 16:
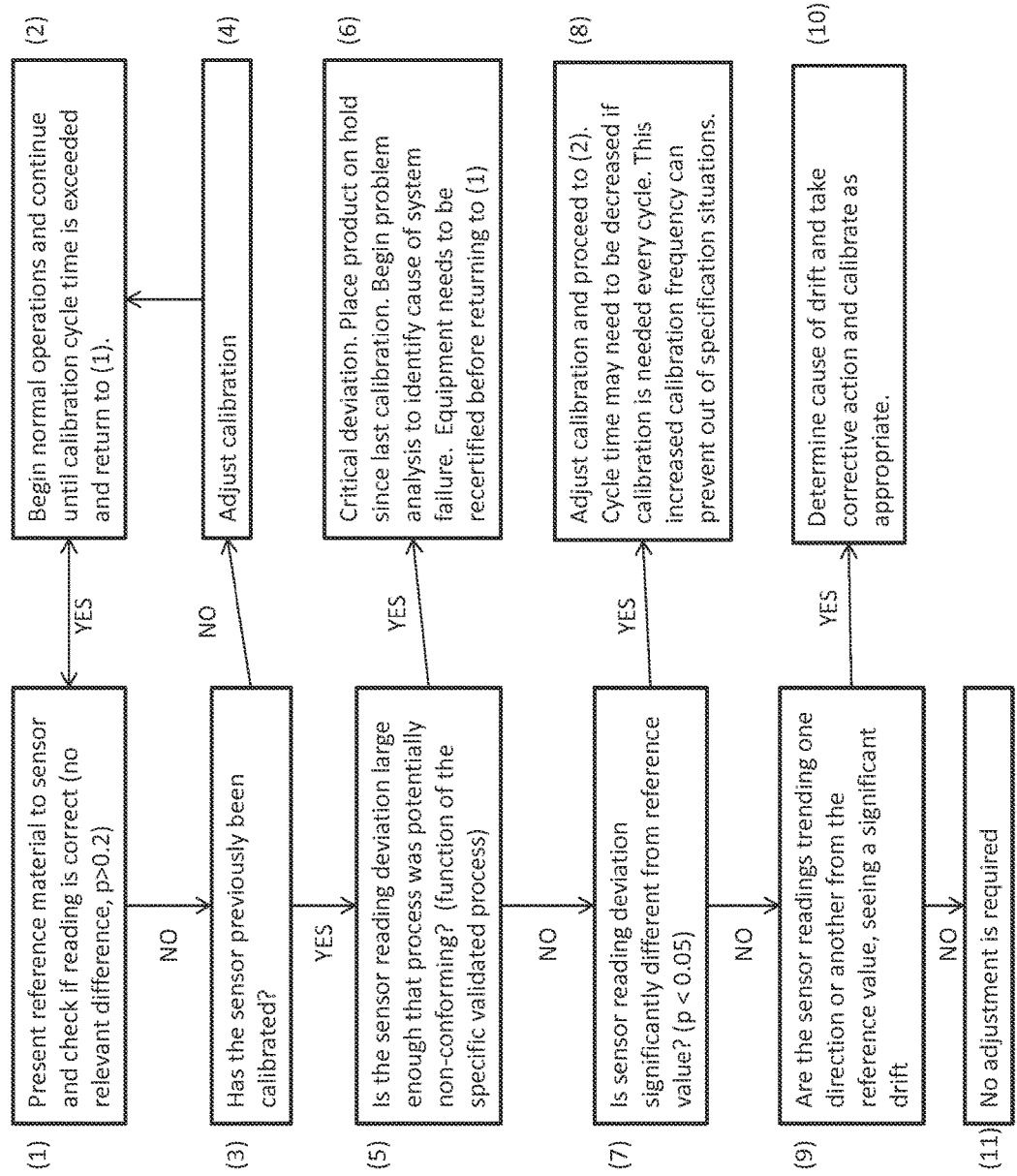
FIG. 16 is a flow chart of a calibration and validation process in accordance with an exemplary embodiment.

FIG. 16 is a flow chart of a calibration and validation process in accordance with an exemplary embodiment. Initially, a reference fluid is presented to a sensor using a calibrator unit, which pumps the reference fluid to the sensor, and the sensor reading is checked to see if it is correct (operation 1). If no relevant difference is found ($p>0.2$), thereby indicating a correct sensor reading, the overall system may begin normal operations (operation 2). When a calibration cycle time expires, the overall system will suspend normal operation and begin a new calibration operation by returning to operation 1. If a relevant difference is found ($p<=0.2$), then a correct sensor reading has potentially not occurred, meaning the sensor is not accurately detecting the known properties of the reference fluid that is passing by the sensor. In this case the system is checked to see if the sensor has been previously calibrated (operation 3). If the sensor has not been previously calibrated, then the system will proceed with adjusting the sensor calibration (operation 4), and once complete, will resume normal operations (operation 2). However, if it is determined that the sensor has been previously calibrated, another determination is required. Specifically, the system will check to see if the sensor reading deviation was large enough indicating that the processing since the last calibration was potentially non-conforming (which is a function of the specified validated process) (operation 5). If a critical deviation is found, such that the sensor reading deviation is large enough that the process was non-conforming, the system will indicate and place the product cleaned during that time period since the last calibration on hold. The system will also begin analysis to identify the cause of the system and/or sensor failure, and an equipment recertification is required before the system is ultimately returned to operation 1 (operation 6). If the sensor reading deviation is not large enough to qualify as a critical non-conforming deviation, the sensor reading is then checked to see if the deviation is considered significantly different from the reference value ($p<0.05$) (operation 7). If the deviation is found to be significantly different, then the sensor calibration is adjusted, and the system will then return to normal operations (operation 8). The cycle time between calibrations may also be decreased based on the difference amount and cycle calibration needed. This increase in calibration frequency can prevent out of specification situations. If the difference is not significant, then the next thing that is check is whether the sensor readings are trending one direction or another from the reference value (operation 9). If a significant enough drift of the sensor readings is shown then a determination of the cause of the drift is made and corrective action and calibration is implemented as appropriate (operation 10). Now, if there is not a significant difference or drift, then the system can make no adjustment (operation 11).

Figure 17:
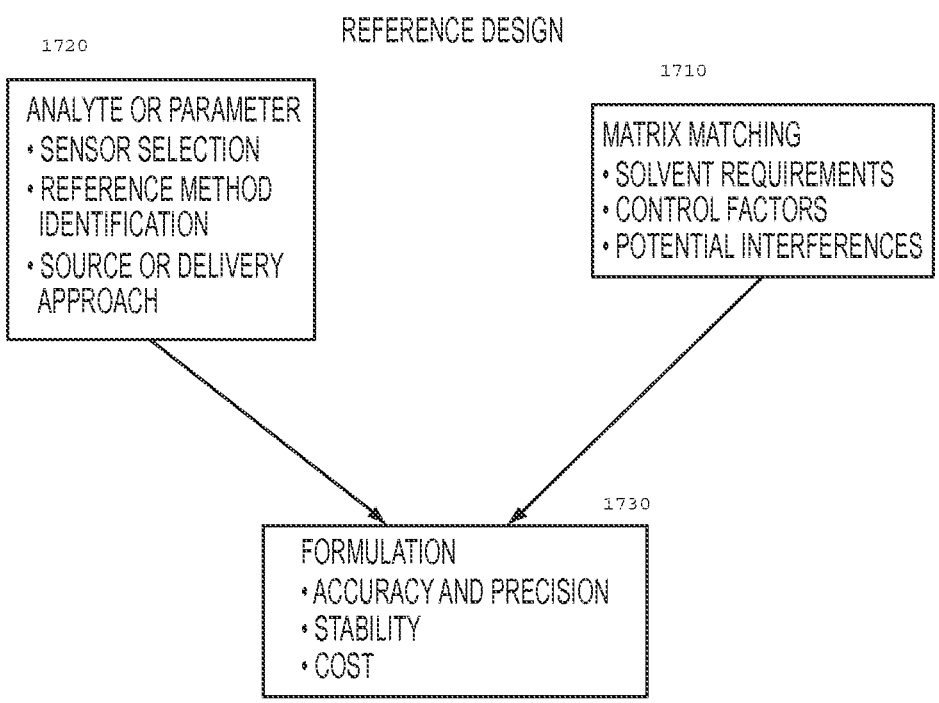
FIG. 17 is a schematic of a reference design process in accordance with an exemplary embodiment.

FIG. 17 is a schematic of a reference design process in accordance with an exemplary embodiment. As shown, when designing a reference fluid for use there are many considerations that impact the reference fluid. For example, sensor selection, reference method identification, and source or delivery approach are considerations that should be taken into account when evaluating an analyte or parameter (1720). Further, solvent requirements, control factors, and potential interferences are considerations that can be handled by matrix matching (1710). Then these considerations, in addition to the other considerations mentioned for evaluating an analyte or parameter, lead to the formulation of the reference where accuracy and precision, stability of the reference fluid, and cost of the reference fluid are all elements that should be addressed when formulating the reference fluid (1730).

Figure 18:
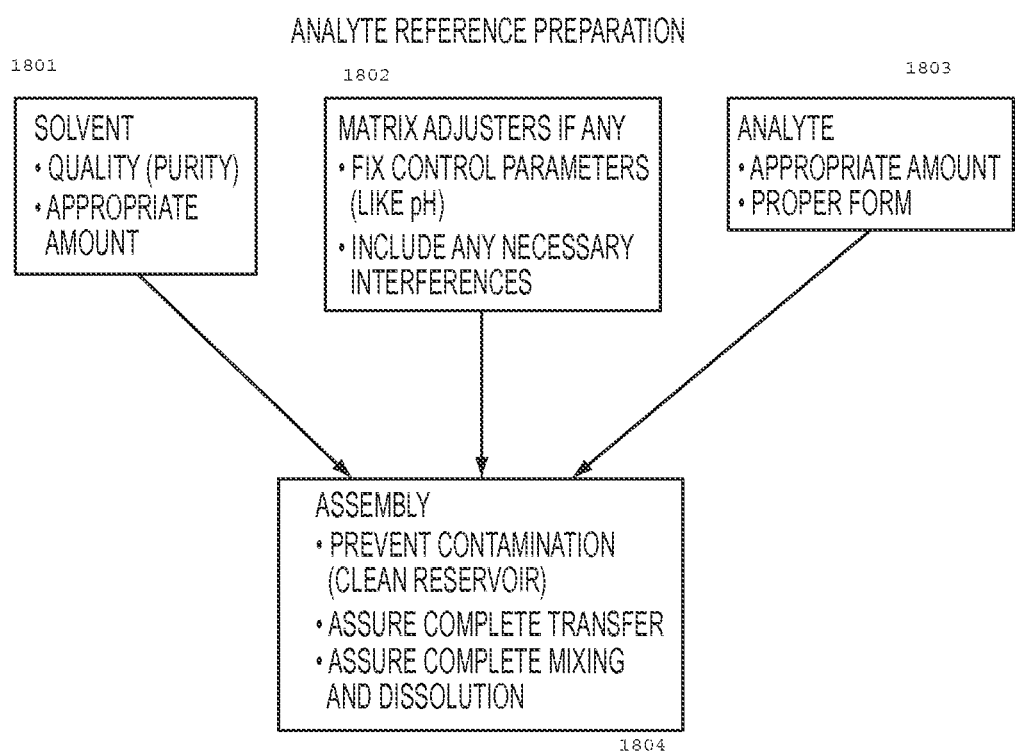
FIG. 18 is a schematic of an analyte reference preparation process in accordance with an exemplary embodiment.

FIG. 18 is a schematic of an analyte reference preparation process in accordance with an exemplary embodiment. Some considerations when selecting and using a solvent include, but are not limited to, solvent quality and/or purity, as well as providing an appropriate amount of solvent (1901). Matrix adjusters may be considered based on such considerations as fixed control parameters (for example pH) and any interferences that should be included (1902). When selecting an analyte is it important to consider at least the proper form and appropriate amount of the analyte (1903). Finally, some considerations to take into account when assembling the reference fluid include, but are not limited to, preventing contamination (for example a clean reservoir), assuring a complete transfer, and assuring complete mixing and dissolution (1904).

In accordance with one or more exemplary embodiments, a calibration process and a validation process as described may be implemented and used in a broad range of applications in and outside of the food industry. For example, the application of the calibration and validation process may be used in produce washing and particularly, shredded lettuce. According to another exemplary embodiment, the calibration process and the validation process fills needs, and therefore may be used in poultry processing where it can be used to validate the control of the composition of sprays, dips, and chilling solutions. These solutions frequently include oxidative materials such as chlorine or peroxyacids that make them applicable exemplary embodiments given the need for galvanic sensors. Additionally, the wash system for raw unprocessed commodities such as tomatoes or melons will benefit from the calibration and validation system and process when there is a process stream that is monitored by sensors. The calibration process and validation process and the calibration and validation system may be used in any number of other systems that use a similar type of sensor.

According to a specific exemplary embodiment, a calibration and validation system may be used to calibrate and validate sensors used with chilling tanks in poultry wash systems. These systems are difficult to manage because of the high lipid content. This challenging environment stresses the performance limits of sensors due to fouling yet is an important area of process control. A lack of control will promote cross contamination and can render the product unsaleable. Accordingly, implementation of the calibration and validation system and processes in this environment is also possible.

Outside the food industry, and in accordance with one or more exemplary embodiments, there are also other operations that require process stream control in which the disclosed system and processes may be implemented. In some cases, it is important to show that constituents are not present. For example, in washing wafers for chip production, very low conductivity water is required. Thus, one is looking for the absence of dissolved solids and ions. However, if the sensor is not working, many wafers will be spoiled. One skilled in the art can readily apply the disclosed calibration and validation system and processes to ensure that the sensor will detect the desired defect, conductivity.

Similarly, in another exemplary embodiment, in a gas flow system, it can be desirable to exclude oxygen in inert gas streams such as helium or argon. Nitrogen streams are somewhat less inert but can also require oxygen monitoring. Here again, insuring that the sensor will respond to the desired defect level and that the process stream meets the process specification. Accordingly, the calibration and validation system and processes may be implemented and used in these environments as well.

While exemplary embodiments have been described with respect to a limited number of embodiments, those skilled in the art, having the benefit of this disclosure, will appreciate that other embodiments can be devised which do not depart from the scope as disclosed herein. Accordingly, the scope should be limited only by the attached claims.

What is claimed is:

1. A food wash sensor calibration system comprising:
a food wash system configured to use a wash fluid and comprising a sensor configured to detect a concentration of an analyte within the wash fluid; and
a food wash reference fluid delivery apparatus comprising:
a mobile frame;
a reference fluid reservoir positioned on and configured to be removable from the mobile frame, the reference fluid reservoir configured to contain a reference fluid with a predetermined concentration of the analyte;
a quick connect coupler configured to removably fluidly couple with the sensor; and
a delivery assembly positioned on the mobile frame, the delivery assembly comprising:
a sensor fluid line configured to provide the reference fluid to the quick connect coupler;
a pump configured to pump the reference fluid from the reference fluid reservoir to the sensor fluid line;
a valve configured to control a fluid volumetric flow rate of the reference fluid through the sensor fluid line; and
a return fluid line configured to provide the reference fluid from the pump to the reference fluid reservoir.

2. The food wash sensor calibration system of claim 1, further comprising a controller programmed to receive a signal indicating a detected concentration of the analyte in the reference fluid from the sensor and to calibrate the sensor based upon a comparison of the detected concentration with the predetermined concentration.

3. The food wash sensor calibration system of claim 1, further comprising a second valve to control the fluid volumetric flow rate of the reference fluid through the return fluid line.

4. The food wash sensor calibration system of claim 1, wherein the sensor comprises a galvanic sensor or a sensor that consumes the analyte.

5. The food wash sensor calibration system of claim 1, wherein the analyte comprises an oxidant, wherein the oxidant comprises chlorine, chlorine dioxide, peroxyacids, hydrogen peroxide, or ozone.

6. The food wash sensor calibration system of claim 1, wherein the reference fluid comprises a predetermined pH and ionic strength, and wherein the sensor is configured to obtain a measurement that is indicative of the predetermined pH and ionic strength.

7. The food wash sensor calibration system of claim 1, wherein the reference fluid comprises a concentrate mixed with water, and wherein the concentrate comprises a dry powder or a stable liquid.

8. The food wash sensor calibration system of claim 2, wherein the controller is programmed to identify a failure of the sensor by comparing the received signal to a sensor failure threshold value.

9. A food wash sensor calibration system comprising:
a food wash system configured to use a wash fluid and comprising a sensor configured to detect a concentration of an analyte within the wash fluid; and
a food wash reference fluid delivery apparatus comprising:
a mobile frame;
a reference fluid reservoir positioned on and configured to be removable from the mobile frame, the reference fluid reservoir configured to contain a reference fluid with a predetermined concentration of the analyte;
a coupler configured to fluidly couple with the sensor; and
a delivery assembly positioned on the mobile frame, the delivery assembly comprising:
a sensor fluid line configured to provide the reference fluid to the coupler;
a pump configured to pump the reference fluid from the reference fluid reservoir to the sensor fluid line; and
a valve configured to control a fluid volumetric flow rate of the reference fluid through the sensor fluid line.

10. The food wash sensor calibration system of claim 9, wherein the coupler comprises a quick connect coupler configured to removably fluidly couple with the sensor.

11. The food wash sensor calibration system of claim 9, further comprising a controller programmed to receive a signal indicating a detected concentration of the analyte in the reference fluid from the sensor and to calibrate the sensor based upon a comparison of the detected concentration with the predetermined concentration.

12. The food wash sensor calibration system of claim 9, the delivery assembly comprising a return fluid line configured to provide the reference fluid from the pump to the reference fluid reservoir.

13. The food wash sensor calibration system of claim 12, further comprising a second valve to control the fluid volumetric flow rate of the reference fluid through the return fluid line.

* * * * *